United States Patent
Kleis et al.

(10) Patent No.: US 9,023,642 B2
(45) Date of Patent: May 5, 2015

(54) METHOD AND APPARATUS FOR A MINIATURE BIOREACTOR SYSTEM FOR LONG-TERM CELL CULTURE

(75) Inventors: Stanley J. Kleis, Houston, TX (US); Sandra K. Geffert, Kingwood, TX (US); Steve R. Gonda, Houston, TX (US)

(73) Assignee: The University of Houston System, Houston, TX (US)

( * ) Notice: Subject to any disclaimer, the term of this patent is extended or adjusted under 35 U.S.C. 154(b) by 1607 days.

(21) Appl. No.: 11/774,550

(22) Filed: Jul. 6, 2007

(65) Prior Publication Data
US 2008/0032380 A1 Feb. 7, 2008

Related U.S. Application Data

(60) Provisional application No. 60/819,325, filed on Jul. 7, 2006.

(51) Int. Cl.
C12M 3/04 (2006.01)
C12N 5/00 (2006.01)
C12M 1/00 (2006.01)
C12M 1/12 (2006.01)
C12M 1/04 (2006.01)

(52) U.S. Cl.
CPC .............. *C12M 29/10* (2013.01); *C12M 23/04* (2013.01); *C12M 23/24* (2013.01); *C12M 29/20* (2013.01)

(58) Field of Classification Search
CPC ...... C12M 23/04; C12M 23/24; C12M 29/10; C12M 29/20; B01L 3/502776; B01L 2200/0636; B01L 2300/0877
USPC .................... 435/297.2, 299.1, 378, 395, 402
See application file for complete search history.

(56) References Cited

U.S. PATENT DOCUMENTS

| 5,153,131 | A | 10/1992 | Wolf et al. |
| 5,496,722 | A | 3/1996 | Goodwin et al. |
| 5,763,279 | A | 6/1998 | Schwarz et al. |
| 6,120,735 | A * | 9/2000 | Zborowski et al. ............. 422/73 |
| 6,632,619 | B1 * | 10/2003 | Harrison et al. ............... 435/7.2 |
| 6,867,040 | B2 | 3/2005 | Helmstetter et al. |
| 2006/0172921 | A1 * | 8/2006 | Freyberg et al. .................. 514/2 |

OTHER PUBLICATIONS

Goodwin, T.J., Jessup JM, Wolf, DA, Spaulding GF, 1993. Reduced Shear Stress: a major component in the ability of mammalian tissues to form three-dimensional assemblies in simulated microgravity. J Cell Biochem 51:Abstract Only.

Levesque, M.J. and Nerem, R.M. 1985,—The elongation and orientation of cultured endothelial cells in response to shear stress. Journal of Biomechanical Engineering. vol. 107, pp.Abstract Only.

* cited by examiner

*Primary Examiner* — William H Beisner
(74) *Attorney, Agent, or Firm* — Robert W Strozier

(57) ABSTRACT

A bioreactor and method that permits continuous and simultaneous short, moderate, or long term cell culturing of one or more cell types or tissue in a laminar flow configuration is disclosed, where the bioreactor supports at least two laminar flow zones, which are isolated by laminar flow without the need for physical barriers between the zones. The bioreactors of this invention are ideally suited for studying short, moderate and long term studies of cell cultures and the response of cell cultures to one or more stressors such as pharmaceuticals, hypoxia, pathogens, or any other stressor. The bioreactors of this invention are also ideally suited for short, moderate or long term cell culturing with periodic cell harvesting and/or medium processing for secreted cellular components.

14 Claims, 31 Drawing Sheets

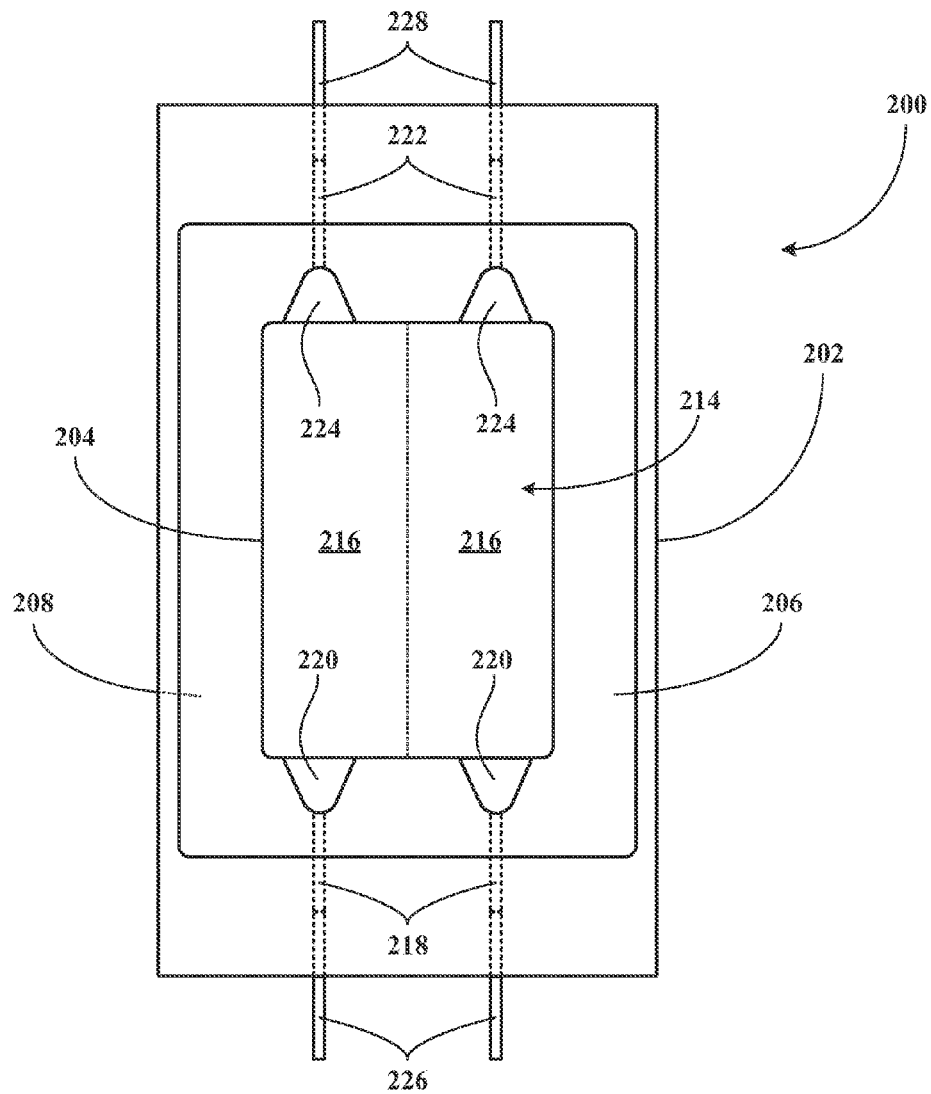
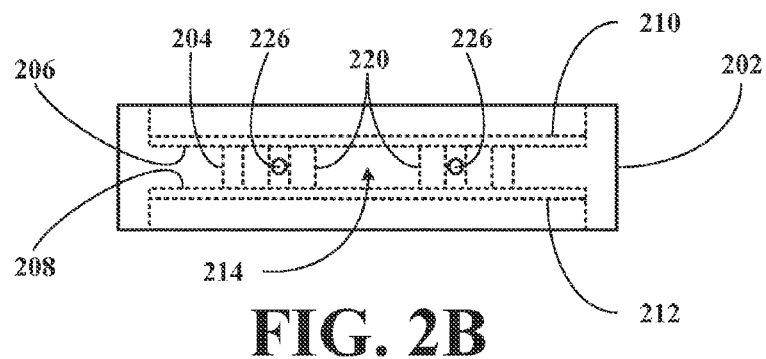
FIG. 2A
FIG. 2B

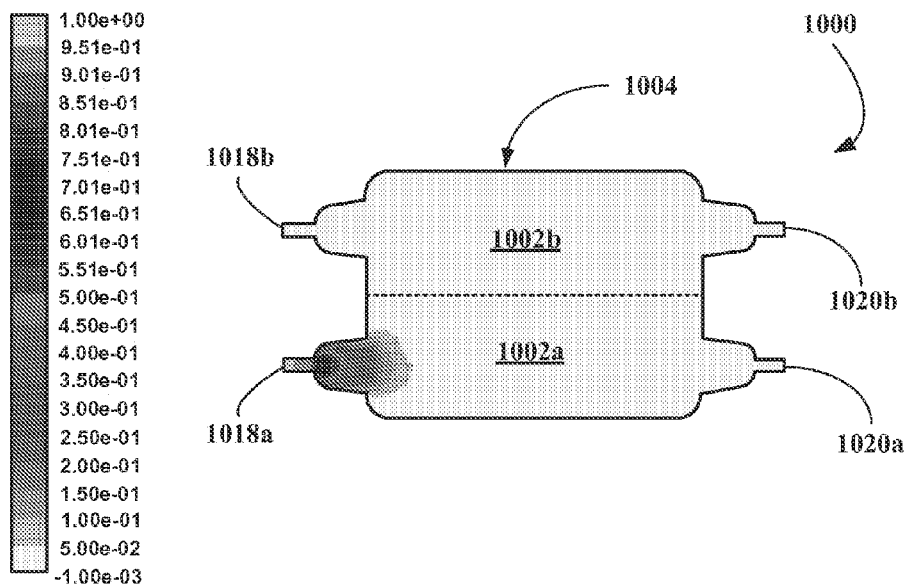
FIG. 10A
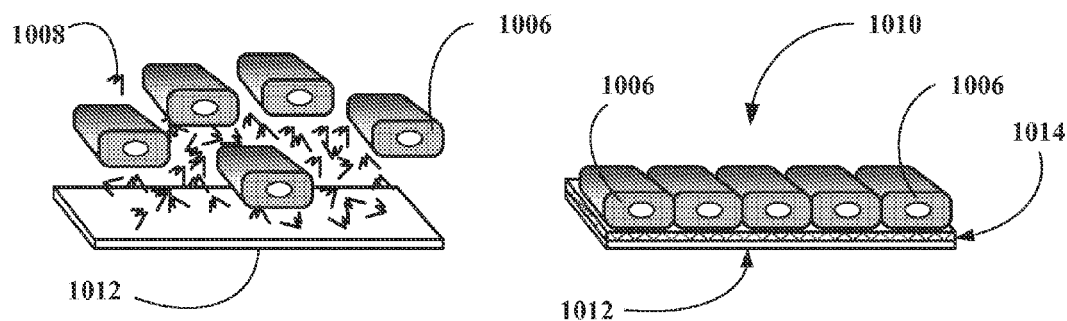
FIG. 10B      FIG. 10C

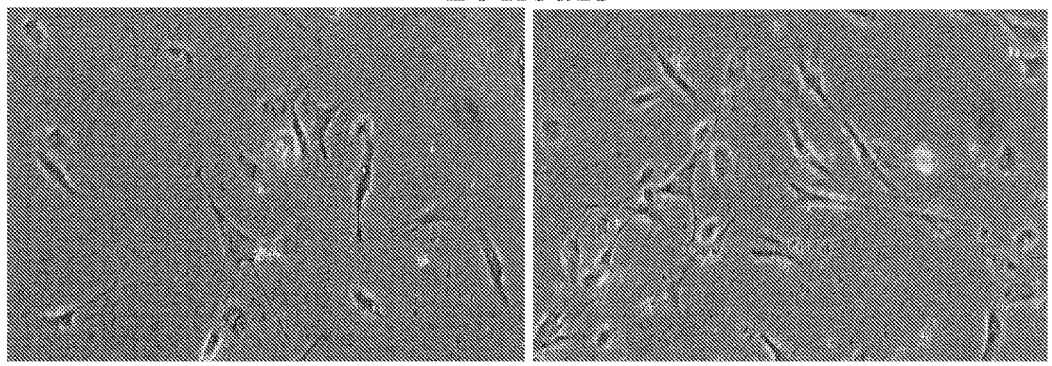
FIG. 18A   FIG. 18B
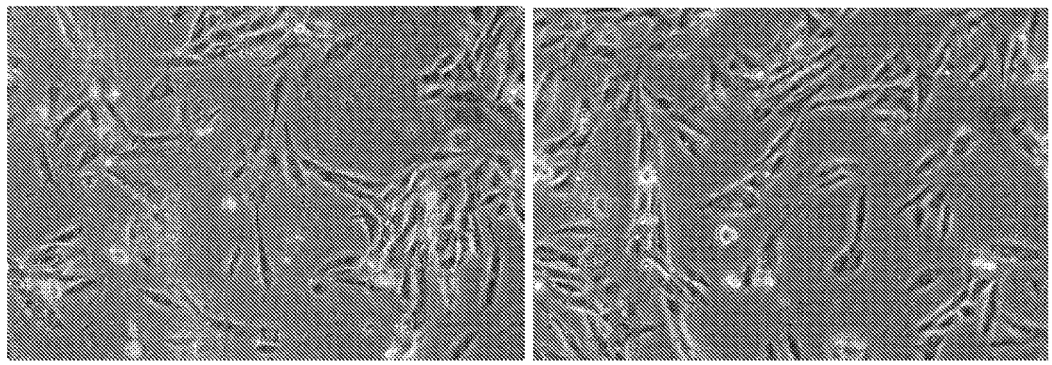
FIG. 18C   FIG. 18D
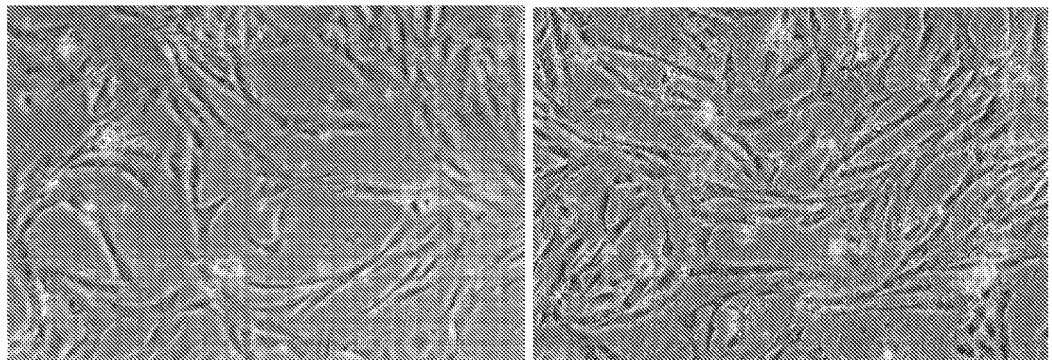
FIG. 18E   FIG. 18F

METHOD AND APPARATUS FOR A MINIATURE BIOREACTOR SYSTEM FOR LONG-TERM CELL CULTURE

RELATED APPLICATIONS

This application claims priority to U.S. Provisional Patent Application Ser. No. 60/819,325, filed 7 Jul. 2006 (Jul. 7, 2006), incorporated herein by reference.

GOVERNMENT INTEREST

Some of the subject matter disclosed in this application was funded to some degree by funds supplied by the United States Government under NASA contract no. 9930-288-01 NCC 9-142.

BACKGROUND OF THE INVENTION

1. Field of the Invention

The present invention relates to a bioreactor apparatus for producing cells, selectively harvesting cells and/or tissues, and/or studying cells and/or tissues in vitro under different conditions over short or long time periods, and methods for making and using same.

More specifically, the invention relates to a bioreactor apparatus for producing cells, selectively harvesting cells and/or tissues, and/or studying cells and/or tissues in vitro under different conditions over short or long time periods, where the apparatus includes a laminar flow chamber having a plurality of cell proliferation zones, each zone having an associated inlet and outlet. The apparatus also includes a fluid handling system and a gas handling system, where the two systems are adapted to seed or inoculate, feed, gasify, harvest, stress, and/or study cells over short or long time periods. The apparatus can also include a housing containing the chamber and systems, where the housing includes pressure, temperature, humidity, etc., control systems. The apparatus can include components for automated and unmanned cell seeding, cell proliferating, cell stressing, cell harvesting and cell monitoring operations under antiseptic conditions and for post harvesting analysis, the apparatus can be associated with a cell fluid dynamic/analysis system, especially a micro-fluidic cell handling and analyzing system. The invention also relates to methods for making and using same.

2. Description of the Related Art

Reliable and efficient cell production is now the central focus in the growing demand for drug development and testing, the creation of artificial organs, the creation of engineered tissue, the production of active proteins made by genetically engineered cells, the production of hormones, antibodies, or enzymes, the preparation of viral vaccines, and the advanced understanding of biological processes. Additionally, efforts have been directed to the understanding of cell growth and behavior upon exposure to stressors, cell-to-cell biocompatibility, tissue healing processes, cell and tissue toxicity, cell apoptosis, cell and tissue chemotaxis, and cell and tissue mechanotaxis. Some of these studies require the simultaneous production of cell cultures within the same bioreactor and in a parallel fashion.

One of the crucial problems associated with cell production is that it is time consuming, expensive, and requires skilled operators. To overcome these barriers, some attempts have been made to manufacture bioreactors and develop methods for optimizing cell production and for studying cell chemotaxis and mechanotaxis.

U.S. Pat. No. 5,153,131 (Wolf et al.) discloses a suspension cell culture system where a culture chamber is rotatable about a horizontal axis and has a vertical large area oxygen transmissible membrane spaced a distance about 0.25 inches less than 1.0 inches from a facing vertical wall surface for effective transmission of oxygen to cells in suspension in the culture chamber. The facing vertical wall surface can be a dialysis membrane for exchange of fresh nutrient from a dialysis chamber with cell waste product in the culture chamber.

U.S. Pat. No. 5,496,722 (Goodwin et al.) disclosed a normal mammalian tissue and the culturing process has been developed for the three groups of organ, structural and blood tissue. The cells are grown in vitro under microgravity culture conditions and form three dimensional cells aggregates with normal cell function. The microgravity culture conditions may be microgravity or simulated microgravity created in a horizontal rotating wall culture vessel.

U.S. Pat. No. 5,763,279 (Schwarz et al.) disclosed an apparatus and method of use for a new simply constructed bioreactor made at least partially of gas permeable materials. The bioreactor is useful for culturing cells and tissues in suspension in a liquid nutrient medium with minimum turbulence. The bioreactor may include ports for easy access to the vessel culture, allowing the growth substrate to be varied for optimum performance. A method for culturing cells using the disclosed bioreactor is also described.

U.S. Pat. No. 6,867,040 B2 (Helmstetter et al.) disclosed an apparatus and methods directed to a perfusion culture system in which a rotating bioreactor is used to grow cells in a liquid culture medium, while these cells are attached to an adhesive-treated porous surface. As a result of this arrangement and its rotation, the attached cells divide, with one cell remaining attached to the substrate, while the other cell, a newborn cell is released. These newborn cells are of approximately the same age, that are collected upon leaving the bioreactor. The populations of newborn cells collected are of synchronous and are minimally, if at all, disturbed metabolically.

Thus, there is a need in the art for an improved bioreactor apparatus for perfusing cells with a medium; controlling an amount of fresh and/or recirculated medium through inlet valves supplying medium to each laminar zone in the bioreactor apparatus; controlling waste collection through an outlet valve; controlling temperature, gas transport, gas exchange, and humidity; inoculating cells through an inoculation port; sampling/assaying cells, supernatant, and cell products; selectively harvesting cells; and selectively harvesting cell products.

SUMMARY OF THE INVENTION

Apparatuses

The apparatus of the present invention provides a laminar flow bioreactor apparatus including a laminar flow cell culture assembly including a laminar flow chamber having a plurality of cell proliferation zones. Each zone is adapted to support cell proliferation. In embodiments involving the use of anchorage cells, each zone includes at least one surface comprising a substrate conducive to cell growth and where each zone includes an inlet and an outlet. However, the substrate can also be a test substrate to determine anchorage propensity, anchorage antagonism, or other substrate effects on cell inoculation, proliferation, harvesting, etc. Each inlet includes a fluid diffuser and each outlet includes a fluid collector.

The apparatus also includes a fluid handling system, where the system supplies medium and/or gas to the zones at a medium flow rate and at a gas concentration sufficient to maintain laminar flow throughout the zones and sufficient to support cell proliferation throughout the zones. In certain embodiments, the chamber has a volume of about 1 mL. In other embodiments, the chamber has a volume less than 1 mL. However, the volume of the chamber can be adjusted to any desired volume, provided that laminar flow is maintained in each of the zones and sufficient gas transport and exchange can occur throughout the zones to maintain all the cells in each zone under substantially the same conditions. It should be recognized that each zone can be supplied with different media and different gases. The zones are adapted to support single cell layers growing on the conducive substrate or to support multiple cells layer, where a first layer is seeded and proliferated onto the conducive substrate and each additional layer deposited onto the previously proliferated layer or to support the preparation of a layer made of a plurality of different cell types, where a first cell type is seeded and proliferated on the conducive substrate and one or more additional cell types are deposited so that the layer comprises a mixture of the cell types. Single cell layers having multiple cell types are ideally suited for studying the effects of stem cells on different cell lines or the effects of cancer cells on different cell lines.

The apparatus can also include a plurality of laminar flow cell chambers and a more sophisticated fluid and gas handling system so that the medium flowing into each zone of each chamber can be the same or different and the cells from each zone of each chamber can be independently or collectively harvested and/or cell products from each zone of each chamber can be independently or collectively collected. The apparatus can also include a sealed and antiseptic housing with the bio-reactor apparatus disposed therein, where the housing includes temperature, pressure, gas, humidify, etc. controller.

The fluid/gas handling system includes inlet valves, outlet valves, an inoculation port, and a cell sampling/assaying port, where the fluid handling system is adapted to perfuse cells in the each zone of each chamber with a medium, control an amount of the medium entering the each zone of each chamber via the inlet valves, and control waste collection via the outlet valves. The fluid/gas handling system and the housing are adapted to control a temperature of the bioreactor apparatus, a pressure in the housing, a humidity in the housing, a gas transport rate into each zone of each chamber, and a gas exchange rate in each zone of each chamber. The fluid/gas handling system is also adapted to inoculate the chamber with cells through the inoculation port, and to sample and assay cells, supernatants, and cell products through the sampling/assaying port, to selectively harvest cells, and to selectively collect cell products. Each chamber is adapted to support a plurality of cell growth regions, where the regions separated one from the other without the need of a physical barrier such as a filters or wall.

Bio-Sensors or Bio-Sentinels

The present invention also provides a monitoring system including a bioreactor apparatus of this invention, where cells in the apparatus are used as bio-sensor or bio-sentinels to evidence hazardous conditions and to alter personnel in potentially hazardous environments of a hazardous condition such as a chemical, biological, physical, radiation, or other hazardous condition.

Systems

The present invention also provides a monitoring system including a bioreactor apparatus of this invention, where cells in the apparatus are exposed to oxygen deprivation, nutrient deprivation, toxins, pathogens and/or mutagenes while monitoring the response of the cells, such as mutations, death, retarded growth, uncontrolled growth, etc.

Methods

The present invention also provides a method including the steps of seeding, producing, and harvesting cells from a bioreactor apparatus of this invention. The method can also include the step of studying cells in the bioreactor apparatus during seeding, producing or proliferating, harvesting and/or studying cell seeding, producing or proliferating, and harvesting. The method can also include the step of monitoring cell seeding, producing or proliferating and harvesting, when exposing cells in the bioreactor apparatus to experimental conditions, where the experimental conditions can include changes in temperature, changes in pressure, changes in humidity, changes in buffers, changes in nutrients, changes in gases and gas mixtures, exposure to pharmaceuticals, exposure to toxins, exposures to mutagenes, exposure to pathogens, or exposure to other harmful or stimulating conditions or additives.

The present invention also provides a method including the steps of seeding, producing, studying and/or harvesting cells using a bioreactor apparatus of this invention. The bioreactor apparatus of this invention is ideally suited for studying: (1) cell chemotaxis, mechanotaxis, apoptosis, artificial organ, skin and other tissue growth, (2) cell production of active proteins, hormones, antibodies, or enzymes, (3) preparing viral vaccines, and (4) drug testing. The method can also include analyzing harvested or collected cells from the apparatus using advanced analytical techniques, tools and equipments.

BRIEF DESCRIPTION OF THE DRAWINGS

The invention can be better understood with reference to the following detailed description together with the appended illustrative drawings in which like elements are numbered the same.

FIGS. 2A&B depict a top view and a side view of an embodiment of a laminar flow chamber of this invention, respectively.

FIG. 10A depicts a

FIGS. 10B&C depict an illustration of cell seeding and proliferating to form a monolayer in a laminar flow chamber of this invention or in reverse, an illustration of cell harvesting a monolayer from a laminar flow chamber of this invention.

FIG. 18A-F depict microphotograph of a zone over a 72 hour period of time evidencing inoculation and proliferation of fetal cardiomyocytes under working conditions.

DETAILED DESCRIPTION OF THE INVENTION

Figure 1A:
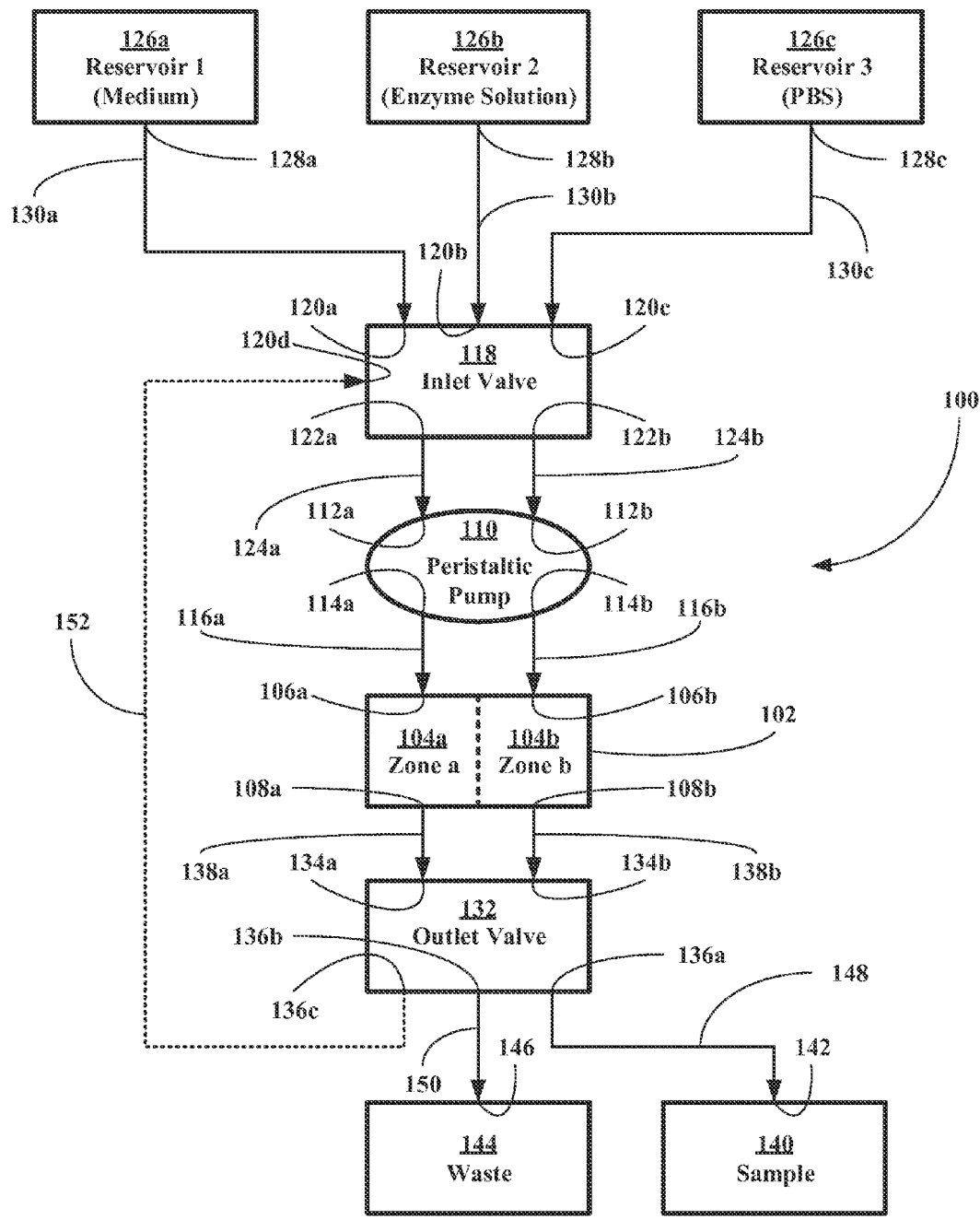
FIG. 1A depicts a block and flow diagram of an embodiment of a bioreactor apparatus of the invention.

The inventors have found that a bioreactor apparatus can be constructed that permits cell seeding or inoculation, cell production, growth or proliferation and cell harvesting or cell product collecting, where the apparatus includes a laminar flow assembly. The assembly includes a laminar flow chamber having a plurality of cell growth regions or zones, where each zone is substantially separated without the need for physical separation elements such as a filter, a barrier, or the like. The chamber is constructed to take advantage of laminar flow of medium into, through and out of the regions or zones so that each laminar flow region or zone can be separately populated, manipulated, controlled, harvested, stressed, etc. without affecting the other regions. Of course, the chamber can be constructed to include an interaction zone between laminar flow zones, where two adjacent laminar regions come into contact. Because the chamber does not include a physical barrier, the chamber is ideally well suited for studying and monitoring interacts between adjacent laminar flow zones such as a monitoring chemical signaling between cells in adjacent laminar flow zones.

The apparatus can also be used to continuously, semi-continuously, periodically, or intermittently harvest cell in the independent regions. The apparatus can also be used for short term, moderate term, and long term proliferation and harvesting of cells of a desired cell line or to study effects of additives on short, moderate or long term culture stability and proliferation. Generally, cell harvesting occurs when proliferation in a zone does not exceed about 95%. In certain embodiments, harvesting occurs when proliferation is a zone does not exceed about 90%. In other embodiments, harvesting occurs when proliferation is a zone does not exceed about 85%. In certain embodiments, harvesting occurs when proliferation is a zone does not exceed about 80%. In certain embodiments, harvesting occurs when proliferation is a zone does not exceed about 75%. In certain embodiments, harvesting occurs when proliferation is a zone does not exceed about 70%. Of course, the proliferation can be greater or smaller depending on the study being performed. It has been found that when proliferation approaches 100%, cultures stability so proliferation is often not taken to much over about 80% before harvesting.

Apparatus

The present invention broadly relates to an apparatus for producing, studying, harvesting, stressing, etc. cells over short, moderate or long periods of time, i.e., an apparatus for preparing short, moderate or long term cell cultures. In certain embodiments, the apparatus includes a sealed and antiseptic laminar flow cell assembly. The assembly includes one laminar flow chamber or a plurality of laminar glow chambers. Each chamber includes a plurality of cell proliferation zones. The chamber includes at least one surface comprising a cell growth conducive substrate disposed on a top or a bottom of the chamber. The chamber can of course include cell growth conducive substrates on both the top and bottom of the chamber. Each zone in each chamber includes an inlet and an outlet. In most embodiment, each inlet includes a diffuser adapted to spread the flow lowering flow velocities as the flow enters the zone, and each outlet includes a collector adapted to reduce turbulent flow as fluid is removed from the zone through the outlet.

The apparatus also includes a fluid handling system. The fluid handling system includes a liquid handling or hydraulic system and a gas handling system. The liquid handling system includes at least one inlet valve connected to the zone inlets and at least one outlet valve connected to the zone outlets, where the inlet valves controls fluid flow to the chamber inlets and the outlet valves control fluid flow out of the chamber. The gas handling system includes a gas supply and regulator for regulating gas flow into the zones. The gas handling system can also include a gas chamber in gas communication with the zones via a gas permeable membrane. The gas handling system can also include values and flow controllers adapted to introduce a gas at a given rate into the medium before or as it is pumped into the zones. The fluid handling system is adapted to perfuse the cells in the zones with a medium, to control an amount of spent (recirculated) medium and/or an amount of fresh medium through the inlet valve(s) into the zones, to control waste collection as spent medium (medium existing the zones) and passes through the outlet valve(s), to control temperature, to control gas transport, to control gas exchange, and to control humidity. The system also includes an inoculation port for inoculating or seeding into the zones of each chamber. The apparatus can also included a sample and/or assay port for sampling or assaying cells in the zones, supernatant coming from the zones, and cell products from the cells in the zones. The apparatus can also be used for selectively harvest cells, and selectively collect cell products.

The plurality of cell zones in each chamber are separated due to the structure of the chamber and the laminar flow maintained in each zone without the need for physical barriers such as filters or other type of physical barrier—the zones are separated by laminar flow. Each zone of each chamber is configured for receiving a culture medium through its inlet and for releasing spent culture medium through its outlet. In most embodiments, the entering medium flow is spread by a diffuser and the exiting medium flow is spread by a collector. The inlets and outlets can also be used to introduce stressors, to introduce pathogens, to introduce toxins, to introduce mutagenes, etc., to harvest cells, to inoculate or seed cells, to inoculate other cell types into a stable or proliferating cell population, or to form multi-layered cell cultures.

The miniature laminar flow bioreactor can be controlled with specially designed or commercial computer software through direct or wireless connections to allow selective seeding, proliferating, and/or harvesting of cells in each laminar zone of each chamber under manual or automated/unmanned control for short, moderate, or long term cell culture studies.

In another embodiment, the bioreactor includes a gas chamber assembly disposed adjacent the gas permeable membrane forming the top or bottom of the chamber and adapted to control gas transport, gas exchange and/or humidity in each zone of the chamber. In most embodiments, the gas chamber assembly supplies a single gas composition to each zone of the chamber, the gas chamber assembly can be partitioned so that each zone is exposed to a different gas composition to study diffusion of gas from one laminar flow zone to an adjacent laminar flow zone via an interaction zone between the zone, which can be designed to be of a desired volume.

In another embodiment, the bioreactor is used to grow suspension cells, anchorage dependent cells, and/or stem cells under controlled conditions designed to grow, harvest and/or study such cells over the short, moderate or long term.

In another preferred embodiment, each chamber can simultaneously support the same or different cell population within each zone, where the zones are laminar flow isolated except for a small and controlled interaction volume at a portion of the chamber where the laminar flow lines in one zone are substantially parallel to the laminar flow lines in an adjacent zone.

In another embodiment, the laminar flow cell culture chamber is sealed to keep gas exchange level at its optimum.

In another embodiment, the laminar flow cell culture chamber is sterilized to minimize external contamination of cells growing within the zone during short, moderate and/or long term cell culture studies, where the and/or means that one zone could support a short term culture, while an adjacent zone could support a moderate or long term culture or any other combination of short, moderate or long term studies.

In another embodiment, the laminar flow cell culture chamber is made of optically transparent walls allowing the device to be used as bench top device sitting on a microscope for the live observation of cell growth and cell behavior upon exposed stressors such as chemical, physical, and/or biological stressors.

In another embodiment, the laminar flow cell culture chamber is coupled with an automated fluid handling system through the inlet and exit valves to control and regulate the perfusion of cells with media, nutrients, saline wash or enzyme treatment, growth factors, drug, hormone, chemotaxis agents, and other substances. In yet another embodiment, the automatic fluid handling system insures the selective harvesting or removal of cells over time to prevent cells from becoming over confluent with dynamic manipulation.

In another embodiment, the automated fluid handling system adjusts pH, temperature, humidity, osmolarity, gas exchange, pressure (normal, hyper or reduced), nutrients levels, cell inoculation ports, sample ports, and selective harvesting of cells, and waste management.

In another embodiment, cells can be selectively removed or harvested from the cell culture chamber. In another embodiment, cells include, but are not limited to, suspension, anchorage dependent, and stem cells either prokaryotic or eukaryotic in type and mixtures or combinations thereof, where mixtures mean a culture of mixed cells and combination means isolated domains of each cell type.

In another embodiment, cells are grown continuously in the laminar flow cell culture chamber. In accordance to another embodiment, the miniature laminar flow bioreactor can generate gradients of various growth factors to aid in the study of chemotaxis, or the migration of cells due to the presence of a chemical gradient. In accordance to yet another embodiment, the miniature laminar flow bioreactor can generate gradients of shear stress to aid in the study of mechanotaxis, or the migration of cells due to the presence of a known shear stress. In accordance to yet another embodiment, the miniature laminar flow bioreactor can generate gradients of various drugs to aid in the study of cell apoptosis.

In another embodiment, the bioreactor can be integrated directly to a micro-analytical system for further analysis of cells or of the product of cells activities generated in the bioreactor, such micor-analytical system generally take advantage of microfluidics to handle cells and cells products.

Component List

One embodiment of a bioreactor of this invention includes:
conditioned gas chamber,
fluid handling system including:
peristaltic pump,
logic inlet and outlet valves, and
fluid reservoirs,
thermal controller,
Peltier-TEC device and fan, and
$CO_2$-Gas Cylinder and regulator.

In other embodiment, the condition gas chamber is replaced by a gas infusion system for generated gasified medium.

The present invention solves some problems inherent in the prior art by providing a device with selective cell removing capabilities that can culture different cell types long term. The bioreactor is a thin, pressure-driven culture chamber with two (or more) inlets and two (or more) outlets. The cover of the reactor consists of a porous respiratory active material to ensure adequate mass transport of $O_2$ and $CO_2$, while the underside consists of a thin microscope cover sheet to allow microscopic imaging or a second porous membrane. The working volume of the bioreactor is approximately 1 mL.

An advanced fluid handling system has been developed to control fresh media infusion and allow for selective cell removal. The fluid handling system consists of two 'logic' valves, a small peristaltic pump (Instech™ OEM P625), and three fluid reservoirs (media, PBS, and Trypsin). The first 'logic' valve allows either the selection of fresh media or PBS to the inlets, or the selective removal of a section of the bioreactor by infusing a proteolytic enzyme (Trypsin) through one inlet and media through the other inlet(s). The lines exiting the bioreactor are draped along the roller bearings of the peristaltic pump and connected to a second 'logic' valve which directs all lines to the waste, or allows for the selection of a specific line to a sample reservoir. Flow passages in the 'logic' valve ensure that only the desired reagent is permitted to enter into the desired line. Since the flow rates required to sustain a micro culture are small, the flow in the central channel will possess classical Hele-Slaw flow characteristics. The flow is essentially a two-dimensional laminar flow created by the thin channel and the low velocity requirement. Laminar flow is characterized by fluid traveling in layers where each element travels smoothly along a simple, well-defined path. This fluid dynamic characteristic will be exploited in anchorage dependent cultures to harvest cells from specific regions of the chamber for analysis without disturbing others. Valving directs harvested cells to a sample reservoir or to waste. In the case of suspension cells, cells are harvested upon the infusion of new media. Incorporated into the miniature culture system is a temperature control system and gas control loop. The inclusion of these two systems will enable the miniature culture system to be autonomous.

Bench Top Application

The miniature culture system can be used autonomously as a bench top bioreactor system. The selective removal and viewing capabilities of the new cell culture system make it an ideal tool to perform and monitor cell migration assays. A precise, reproducible section of cells can be removed from the cell culture device by introducing an enzymatic protein to a strip of cells. Cells exposed to the enzymatic protein will dissociate from the growth substrate and be removed from the culture device upon infusion of new media. The design of the bioreactor housing and control system enable the system to sit directly on top of a microscope stage. This is ideal for phase or fluorescence time-lapse microscopy. Both environmental (i.e. chemical) and mechanical (i.e. shear) parameters could be examined in the bioreactor, and thus aid in determining factors that might have a significant impact on directed cell migration and/or wound healing.

Integration with Micro-Analytical Device for In Situ Monitoring

The miniature culture system is a novel device that may advance the development of micro analytical tools such as biological sentinels, biosensors, and lab-on-a-chip devices. Integrating the autonomous miniature culture system with a micro-analytical device provides one with a powerful biological tool since cells can be cultured long term and released directly into an analytical tool without the need for human interaction. The analytical device can be tailored to perform a vast array of assays from monitoring changes in intracellular proteins or DNA structure to detecting chemical signals in response to exposed stressors over time. The integration of these two systems will enable the development of a completely autonomous miniature cell culture and analytical system. Due to the size and volume requirements, the device will significantly reduce the reagent requirements for cell culture. The autonomous system can be tailored for either laboratory bench top applications or for studies in remote and/or difficult environments (e.g. extra-terrestrial or low gravity studies).

Flow visualization studies were performed using the above embodiment. The capabilities bioreactor and fluid handling system were tested. Food coloring was used to mimic different cell culture reagents during different cell culture processes. Flow visualization demonstrated the effectiveness of the miniature bioreactor to perform cell media infusion, PBS flush, dye/stain infusion, cell inoculation procedures, and enzymatic dissociation. The flow demonstrated its Hele-shaw characteristics and the reagents did not mix. The area chosen for selective removal was correctly distributed into the sample port while the other two regions were correctly circulated into the waste bottle.

Numerical studies were completed to examine different geometries before fabricating and experimenting with the miniature device.

A prototype bioreactor was fabricated after studying the results of flow visualization studies.

Initial studies demonstrated that BHK-21 cells could be cultured either on the membrane or on the glass top for several weeks at a time.

A second prototype bioreactor was also fabricated, and the bioreactor was tested for bench top readiness so that it could be used as a plug and play cell culturing apparatus in microfluidics cell analyzer system.

Numerical shear level and chemotaxis (scalar transport) studies were performed in Fluent™.

The invention includes a miniature bioreactor vessel and fluid handling system to complement current micro analytical systems or other diagnostic tools for long term cell studies.

The miniature bioreactor system is comprised of a bioreactor, fluid handling system, and a temperature controlled conditioned air chamber. The miniature bioreactor system cultures both suspension and anchorage dependent cells (either procaryotic or eukaryotic in type), in normal, micro, or hypo gravity, and can be directly integrated with a micro analytical device for in situ analysis of cells and soluble factors. The fluid handling system not only provides the culture region with nutrients and waste removal, but enables cells to be selectively removed over time for real time long term cell culture studies.

Due to the size of the bioreactor, it would make an 'ideal' complete bench top cell culturing tool minimizing the need for expensive equipment and reagents. The culture device can be computer controlled reducing the time and effort of the investigator and uncertainty in the results. The device can culture both anchorage dependent and suspension cells, either prokaryotic or eukaryotice in type. Hence, the apparatus may be utilized for many different cellular research and commercial applications.

The miniature culture system is a novel device that may advance the development of micro analytical tools such as biological sentinels, biosensors, and lab-on-a-chip devices. Integrating the autonomous miniature culture system with a micro-analytical device provides one with a powerful biological tool since cells can be cultured long term and released directly into an analytical tool without the need for human interaction. The analytical device can be tailored to perform a vast array of assays from monitoring changes in intracellular proteins or DNA structure to detecting chemical signals in response to exposed stressors over time Finally, the miniature system could be exploited to perform popular migration assays. The fluid handling system enables the presence of a chemical gradient to study the response of cells to different growth/healing chemicals. Both environmental and mechanical parameters could be examined in the bioreactor and thus aid in determining factors that might have a significant impact on wound healing.

A prototype miniature bioreactor system has been designed and fabricated to possess selective cell removing capabilities. Initial studies demonstrate selective cell removal capabilities and outline protocols for the use of the mini-culture system. The new system was used to investigate fibroblast cell migration under normal culture conditions. A strip of cells are removed by implementing selective cell removal protocols in the mini-bioreactor. Images of cell migration into the harvested region are captured with a Nikon TMS time-lapse phase contrast microscope and digitized to determine migration times. Additionally, the system can be used to study cell culture response to a gradient of a known chemo-attractant. Thus, the system can be used to study the ability to culture contact-inhibited, anchorage-dependent cells for an extended period of time, determine the limits and repeatability of the device, and demonstrate the ability to exploit the miniature culture system for ground based migration/chemotaxis assays.

From Presentation

Technical Information

The working volume of the chamber used in the experimental section as 1 mL. The bioreactors are pressure driven and are based on a Hele Shaw type system, supporting laminar flow evidenced by extremely low shear under normal working conditions. The bioreactor can be equipped with a controlled gas chamber separated from the growth zone via a gas permeable membrane. The conditioned gas is supplied from a 5% $CO_2$ pressurized tank, where the amount of gas supplied is verified using a Fryrite Gas Analyzer. Gas exchange ($CO_2$ and $O_2$) is achieved via a gas permeable membrane between the bioreactor growth zone and the conditioned gas chamber. Temperature is maintained externally with a Peltier element and a PID controller. A fluid handling system controls the fluids entering and leaving the zones of the bioreactor via inlet and outlet valves. The fluids are supplied from reservoirs via the valve, where the valves are used to select make up of the fluid being supplied. In many embodiments, the zones are supplies with a medium that include a medium carrier having appropriate nutrients from a medium reservoir to this can be added proteases for harvesting from a protease reservoir or an agent to induce a specific effect.

In certain embodiments, the bioreactor represents a miniature system and is mobile and has minimal reagent use for automated and unmanned operation in remote location such as space, mines (bio-sensors), nuclear power plants (bio-sensors), chemical plants (bio-sensors), etc. The bioreactors of this invention can be used for AD or Suspension Cells, for short, moderate or long term cell cultures. The bioreactors of this invention is ideal for the following types of studies: cell migration studies; chemotaxis studies, and co-culture—interface studies.

The bioreactors of this invention is also ideally well suited for bench top miniature long term culture unit, which can operate as a plug and play unit, meaning that the bioreactors of this invention can be directly integrated into a bench top unit. The bioreactors represent an universal system for culturing all cell types with minimal use of expensive reagents. The chamber are microscope-ready ideal for morphological studies, cell migration/chemotaxis studies or to harvest cells to prevent over-confluence. The bioreactors of this invention can be efficiently integrated with microfluidics device permitting construction of autonomous bioreactor systems, permitting monitoring with or without control feedback with the capability to remove sections of cells for in situ analysis using remote sensing.

Suitable Reagents

Suitable medium for use in this invention include, without limitation and depend on the cells being cultured, any cultures medium now used or to be developed to support short, moderate, or long term cells cultures. One of ordinary skill in the art will recognized that there are many cells and cell lines each having their own tailored growth medium and new grow media are being developed daily. The bioreactors of this invention can be operated using any growth medium required for the type of cell being cultured.

Suitable cells of culturing with the bioreactors of this invention include, without limitations, prokaryotic cells, eukaryotic cells (plant, animal or fungi), stem cells (any organism that produces stem cells), mixtures or combinations thereof. Although the bioreactors are set up for cell growth and proliferation, the bioreactors can also be used to studies viruses and viral infections, by growing a stable cell population and then infecting it with a virus and monitor the effects.

Introduction

Micro-fluidics is a developing field that possesses great promise for enhancing cell biology analysis and remote monitoring/sensing capabilities, especially for applications being developed by and for NASA. In addition to a significant decrease in payload requirements of micro-fluidic devices, the devices are particularly well-suited for the challenges and limitations presented in biochemical analyses required for remote monitoring. Since mammalian cells respond chemically and physically to their environment, animal cells are being considered for use as biological sentinels (early warning of hazardous environmental factors for humans in space) and remote monitoring tools. To support this effort, a novel miniature culture system (<1 mL) has been designed for the long-term culture of both anchorage dependent and suspension cells.

Animal cells have strict demands on their growth conditions including pH, temperature, oxygen, and nutrient supply. These demands must be met in the design of a culture system, especially a miniature culture system, while maintaining a low shear environment. In addition, the system should have the capability to harvest a cell population is required to prevent the cells from losing their ability to divide and proliferate. The system should also have the capability to selectively sample cells over time to enable monitoring of alterations in cell gene expression or production during long term missions or in extraterrestrial environments or to monitor cells subjected to a stress factor or exposed to other cells types.

Miniature Bioreactor and Flow Circuit Development

A miniature flat plate bioreactor chamber was designed for short, moderate, and long term cultures of both anchorage dependent and suspension cells, either prokaryotic or eukaryotic in type. The miniature chamber can be constructed with a volume of <1 mL, but the chamber can be of any desired volume.

The inventors constructed an embodiment of a chamber from a delrin block about 0.635 mm (0.25 in). The block was milled with a square or rectangular through-hole about 2 cm×2 cm. Of course, an ordinary artisan should recognize that the bio-reactor can be constructed out of any suitable material and can be constructed to be of any desired size and shape. Square recesses were fabricated in the top and bottom. At least one of the recesses is adapted to receive a transparent member. In certain embodiments, especially embodiments where needed gases are transmitted with the medium (dissolved in the medium), the chamber includes two transparent members, one situated in the top recess and the other in the bottom recess. In certain embodiments, a thickness or a height of the chamber, the gap between the top member and the bottom member, is about 2 mm. However, larger and smaller thicknesses can be used. Thus, the thickness can range from about >one cell thickness to ten of millimeters. In certain embodiments, the thickness ranges from about a cell thickness to about 10 mm. In other embodiments, the thickness ranges between about 0.1 mm and 5 mm. In other embodiment, the thickness ranges between 0.5 mm and about 4 mm. In other embodiments, the thickness ranges between about 1 mm and about 3 mm. The transparent member is then sealed in place to form one interior surface of the chamber. Optionally, the chamber can include one transparent member and one transparent, gas permeable membrane, where the membrane can be disposed in the top recess or the bottom recess. A suitable gas permeable membrane such as a gas permeable, polystyrene matrix membrane can be used, but any transparent, gas permeable membrane can be used as well. The transparent member can be glass cover-slips, but any transparent member can be used as well. The transparent members or the transparent member and the membrane are secured using a biocompatible silicone adhesive such as Dow Corning, RTV 111, but any biocompatible adhesive can be used as well.

In certain embodiments, the transparent membrane is transparent of a desired frequency range of electromagnetic radiation (light). In most embodiments, the frequency range is visible light, but in other embodiments, the frequency range could be IR, near IR, and UV. Of course, the bioreactors of this invention can also be equipped with filters that narrow the range of light being viewed or transmitted through the zones of the chamber. Additionally, each zoned can have a different filter and a different range of transparency.

The inventors then milled two cylindrical inlets and two cylindrical outlets form opposite side of the box into the chamber. The inlets and outlets are adapted to receive tubes for attaching supply and release conduits thereto. The inventors used 0.112 mm (OD) diameter stainless tubes, but any tube can be used; provided, of course, that tubes are biocompatible. In certain embodiments, the inlets include small diffusers formed in the chamber at chamber ends of the inlets to lower inlet fluid velocities, to spread a fluid flow profile and to prevent the formation of fluid jets near the inlet. In other embodiments, the inlets include the diffusers, while the outlets includes collectors to lower outlet fluid velocities, to spread a fluid flow profile and to prevent the formation of fluid jets near the outlet.

Referring now to FIG. 1A, a block diagram of an embodiment of a laminar flow bioreactor apparatus of this invention, generally 100, is shown to include a laminar flow, cell culture chamber 102 having a first laminar flow cell proliferation zone 104a and a second laminar flow cell proliferation zone 104b. The two zones 104a and 104b include zone inlets 106a&b, and zone outlets 108a&b. Upstream of the chamber 102 is a peristaltic pump 110 having two inlet ports 112a&b and two outlet ports 114a&b. The pump outlet ports 114a&b are connected by flow conduits 116a&b to their respective zone inlets 106a&b. The dashed line separating the zones 104a and 104b is only to aid in visualization and does not represent a physical barrier of any kind, because the zones are laminar flow isolated.

Upstream of the pump 110 is an inlet valve 118 having three inlet valve inlets 120a-c and two inlet valve outlets 122a&b. As well be shown and discussed herein, the inlet valve 118 can include additional inlets. The inlet valve outlets 122a&b are connected by flow conduits 124a&b to their respective pump inlet ports 112a&b. Upstream of the inlet valve 118 are three reservoirs 126a-c, each having an outlet 128a-c. The reservoir outlets 128a-c are connected by flow conduits 130a-c to their respective inlet valve inlets 120a-c.

Downstream of the chamber 102 is an outlet valve 132 having two inlets 134a&b and three outlets 136a-c, one outlet 136c is optional and is used when medium recirculation is desired. The zone outlets 108a&b are connected by flow conduits 138a&b to their respective outlet valve inlets 134a&b. Downstream of the outlet valve 132 is a sample collection container 140 having a sample inlet 142 and a waste container 144 having a waste inlet 146. The outlet valve outlet 136a is connected by a flow conduit 148 to the sample inlet 142. The outlet valve outlet 136b is also connected by a flow conduit 150 to the waste inlet 146. The optional outlet valve outlet 136c is connected by an optional flow conduit 152 to a recycle inlet valve inlet 120d, where the amount of fresh and recycled medium is controlled by the valve 118. However, flow regulators or controllers can also be used to improve flow control.

Figure 1B:
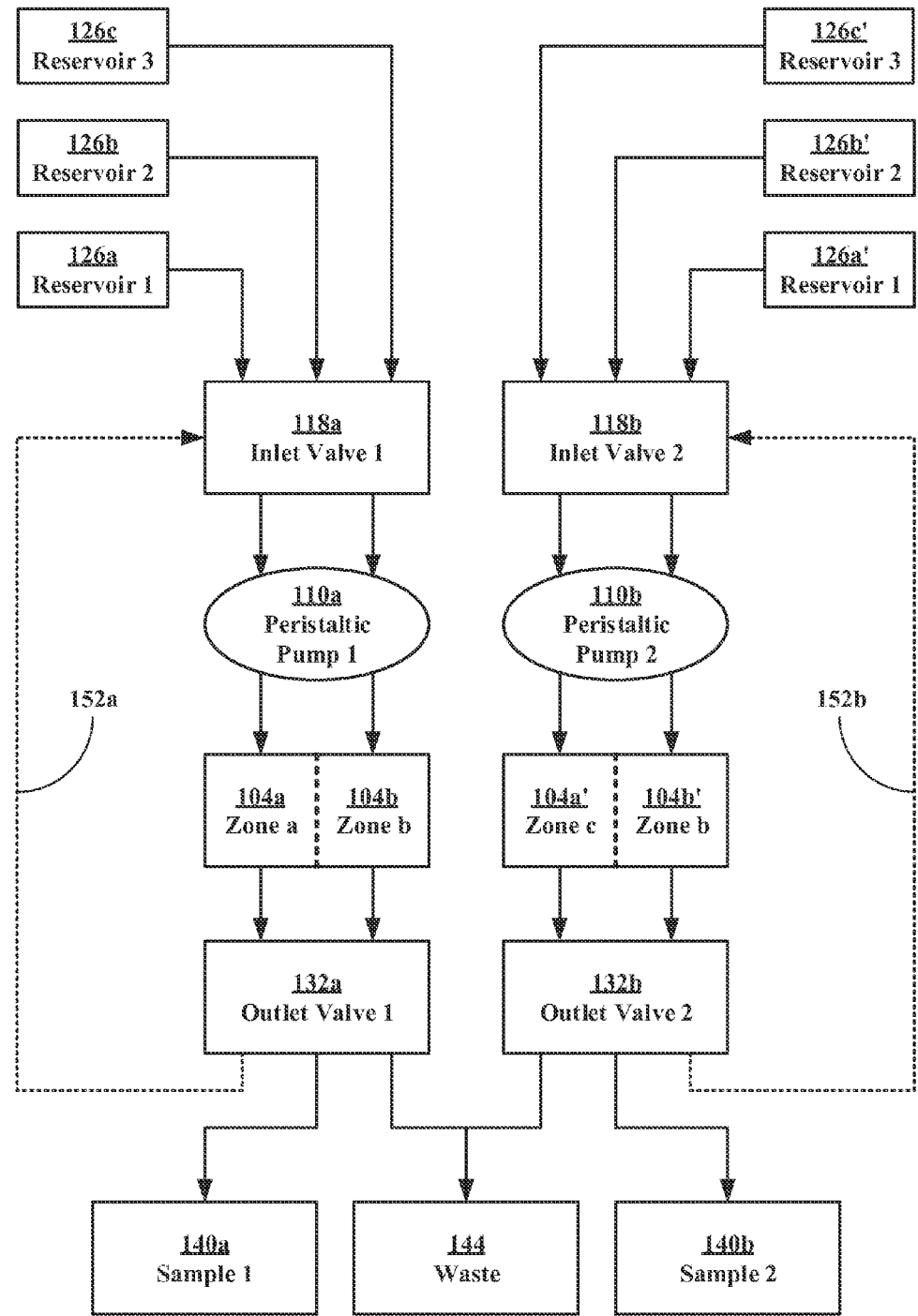
FIG. 1B depicts a block and flow diagram of another embodiment of a bioreactor apparatus of the invention.

Referring now to FIG. 1B, a block diagram of another embodiment of a laminar flow bioreactor apparatus of this invention, generally 100, is shown to include two laminar flow, cell culture chambers 102a&b having first laminar flow cell proliferation zone 104a&a' and a second laminar flow cell proliferation zone 104b&b'. Upstream of the chambers 102a&b are two peristaltic pumps 110a&b.

Upstream of the pumps 110a&b are inlet valves 118a&b. Upstream of the inlet valves 118a&b are reservoirs 126a-c and 126a'-c'. Downstream of the chambers 102a&b are outlet valves 132a&b. Downstream of the outlet valves 132a&b are sample collection container 140a&b and a waste container 144. Again, if medium recycling is contemplated, then the apparatus 100 also include recycle conduits 152a&b.

The components are interconnected by conduits connecting outlets of one component to inlets of an downstream components and connecting inlets of one component to outlets of an upstream component. Due to space constraints, the conduits, inlets and outlets are not labeled, but are clearly understood by the conduit starts and stops.

In the two embodiments, the arrows associated with the conduits evidence the direction of fluid flow into and out of each component.

The two bioreactor apparatus embodiments 100 of this FIGS. 1A&B can be of any size. In certain embodiments, the bioreactor apparatus 100 is a miniature laminar flow bioreactor, where the chamber 102 has a volume of about 1 mL or less. The bio-reactor apparatus 100 can comprise a closed and aseptic environment adapted to grow cells that include, but are not limited to, prokaryotic or eukaryotic suspension cells, prokaryotic or eukaryotic anchorage dependent cells, and/or stem cells under laminar flow conditions. The and/or is includes to address cultures comprising a mixture of cells, such as stem cell introduction into a stable cell culture to study stem cell integration or stem cell effects, and to address cultures comprising a combinations of cells such as multilayer cell cultures, where each layer comprises a different cell line or type, or isolated islands of cells. The laminar flow bioreactor 100 can be fully automated so it can run autonomous, allowing its use and operation in remote locations or in harsh and dangerous environments including space environments.

Referring now to FIGS. 2A&B, an embodiment of a chamber of this invention, generally 200, is shown to include a body 202. The body 202 includes a rectangular or square aperture 204 therethrough. The apparatus 200 also includes a top recessed area 206 and a bottom recessed area 208. The apparatus 200 also includes a top transparent member 210 and a bottom transparent member 212 defining a volume 214. The volume 214 includes two laminar flow zones 216. Each zone 216 includes an inlet 218 having a diffuser 220, where the diffuser 220 is adapted to spread a flow of fluid as it enters its corresponding zone 216. Each zone 216 also includes an outlet 222 having a collector 224, where the collector 224 is adapted to reduce flow constrictions of fluid as it exits its corresponding zone 216. The inlets 218 are fitted with inlet tubes 226 and the outlets 222 are fitted with outlet tubes 228. The tubes 226 and 228 are adapted to be receive tubing used as conduits to connect the inlets and outlets to inlet and outlet valves, respectively as described herein. Although in FIG. 2B, the diffusers 220 are shown to extend the entire height of the volume 214, the diffusers 220 can have a height less than the entire height of the volume 214. The same is also true of the collectors 224. The height of the diffusers 220 and collectors 224 must be sufficient to spread the fluid flow into or out of the zones 216 to prevent jetting or channeling and to maintain laminar flow conditions during cell seeding and proliferation. Of course, for harvesting, fluid conditions can be increased as needed to affect a given harvesting rate. The dividing dashed line through the volume 214 is included to show the laminar flow separation of the zones 216, it is not a physical barrier, but simply to aid in the visualization of the zones 216, because the zones are laminar flow isolated.

Figure 2C:
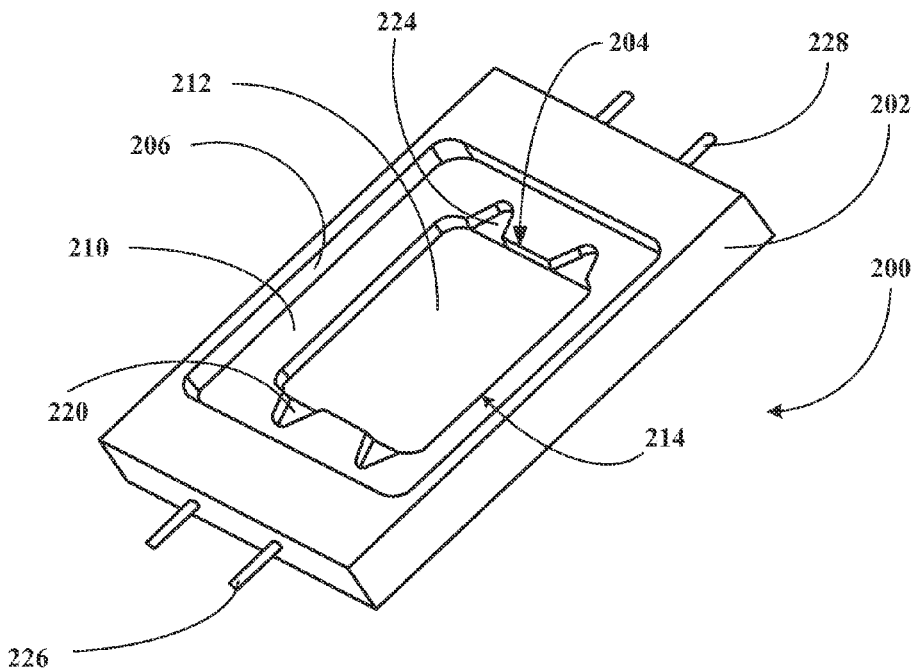
FIG. 2C depicts a 3D rendering of the chamber of FIGS. 2A&B.
Figure 2D:
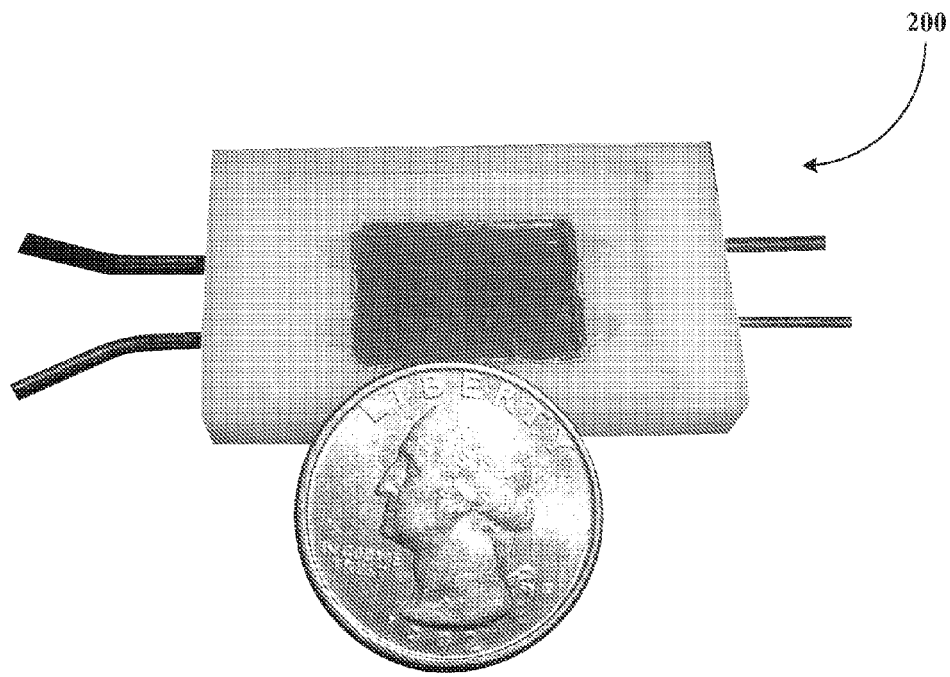
FIG. 2D is a photograph of the chamber of FIGS. 2A&B relative to a quarter.

Referring now to FIGS. 2C&D, a perspective 3D rendering of the apparatus 200 is shown with appropriate features labeled as described above. FIG. 2D shows the relative size of the chamber 200 compared to a quarter.

Figure 2E:
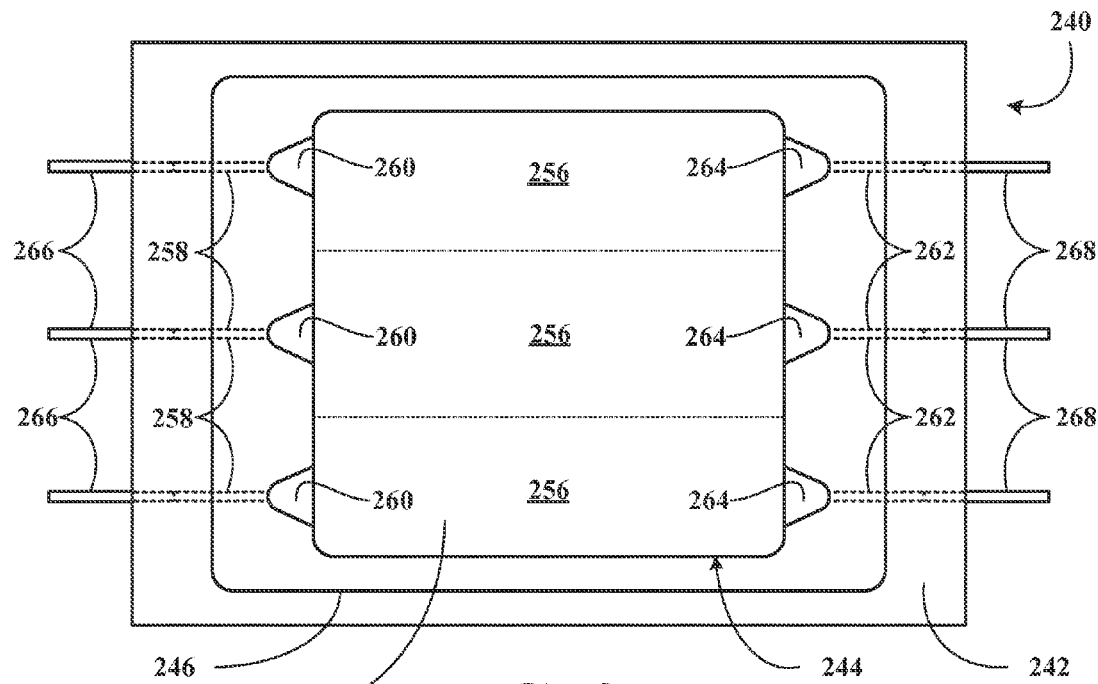
FIG. 2E depicts a top view of another embodiment of a laminar flow chamber of this invention having three laminar flow isolated zones.

Referring now to FIG. 2E, an embodiment of a chamber of this invention, generally 240, is shown to include a body 242. The body 242 includes a rectangular or square aperture 244 therethrough. The apparatus 240 also includes a top recessed area 246 and a bottom recessed area (not shown). The apparatus 240 also includes a top transparent member (not shown) and a bottom transparent member (not shown) defining a volume 254. The volume 254 includes three laminar flow zones 256. Each zone 256 includes an inlet 258 having a diffuser 260, where the diffuser 260 is adapted to spread a flow of fluid as it enters its corresponding zone 256. Each zone 256 also includes an outlet 262 having a collector 264, where the collector 264 is adapted to reduce flow constrictions of fluid as it exits its corresponding zone 256. The inlets 258 are fitted with inlet tubes 266 and the outlets 262 are fitted with outlet tubes 268. The tubes 266 and 268 are adapted to be receive tubing used as conduits to connect the inlets and outlets to inlet and outlet valves, respectively as described herein. The dividing dashed line through the volume 254 is included to show the laminar flow separation of the zones 256, it is not a physical barrier, but simply to aid in the visualization of the zones 256, because the zones are laminar flow isolated.

Figure 2F:
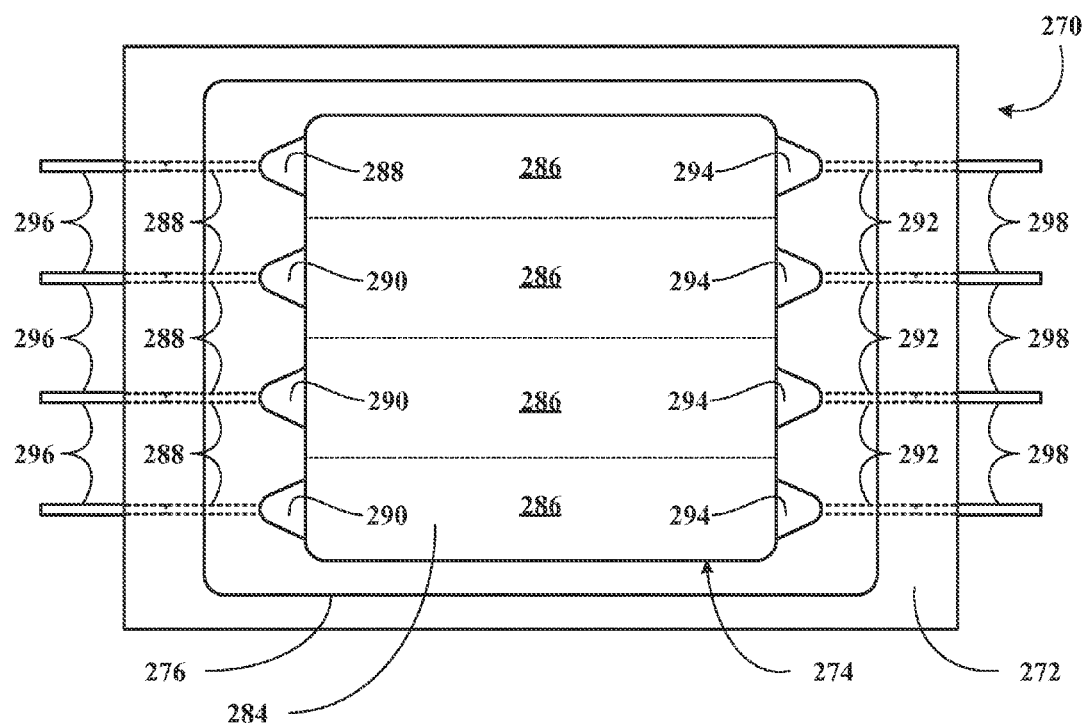
FIG. 2F depicts a top view of another embodiment of a laminar flow chamber of this invention four laminar flow isolated zones.

Referring now to FIG. 2F, an embodiment of a chamber of this invention, generally 270, is shown to include a body 272. The body 272 includes a rectangular or square aperture 274 therethrough. The apparatus 270 also includes a top recessed area 276 and a bottom recessed area (not shown). The apparatus 270 also includes a top transparent member (not shown) and a bottom transparent member (not shown) defining a volume 284. The volume 284 includes four laminar flow zones 286. Each zone 286 includes an inlet 288 having a diffuser 290, where the diffuser 290 is adapted to spread a flow of fluid as it enters its corresponding zone 286. Each zone 286 also includes an outlet 292 having a collector 294, where the collector 294 is adapted to reduce flow constrictions of fluid as it exits its corresponding zone 286. The inlets 288 are fitted with inlet tubes 296 and the outlets 292 are fitted with outlet tubes 298. The tubes 296 and 298 are adapted to be receive tubing used as conduits to connect the inlets and outlets to inlet and outlet valves, respectively as described herein. The dividing dashed line through the volume 284 is included to show the laminar flow separation of the zones 286, it is not a physical barrier, but simply to aid in the visualization of the zones 286, because the zones are laminar flow isolated.

Figure 3A:
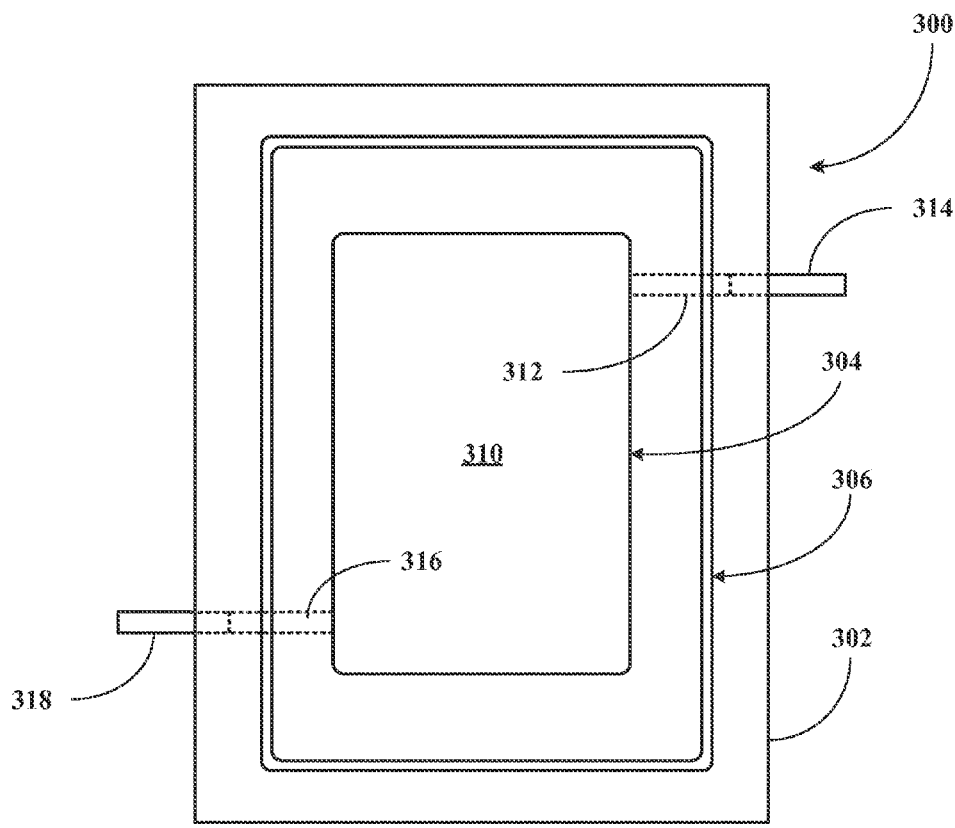
FIGS. 3A&B depict a top and side view of an embodiment of a controlled gas chamber for use with the chamber of FIGS. 2A&B.
Figure 3B:
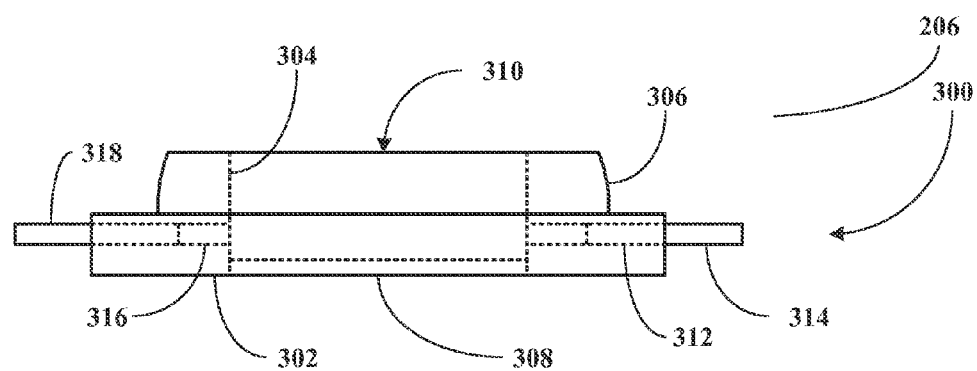

Referring now to FIGS. 3A&B, an embodiment of a gas supply and control chamber apparatus of this invention, generally 300, is shown to include a body 302. The body 302 includes a rectangular or square aperture 304 therethrough adapted to correspond to the aperture 204 of the chamber 200 of FIG. 2A. The apparatus 300 also includes a raised bottom portion 306 adapted to be inserted into the top or bottom recessed area 206 or 208 of the chamber 200 of FIG. 2A, depending on which member 210 or 212 is a gas permeable membrane. The raised bottom portion 306 is shown here slightly tapered in a convex taper, but can be substantially straight. The apparatus 300 also includes a top transparent member 308 so that the chamber can be observed through the gas chamber apparatus and forming a gas cavity 310, which when the gas chamber apparatus 300 is properly situated in a recessed area of the chamber 200 is defined by the aperture 304, the member 210 or 212 and the member 308. The apparatus 300 also includes a gas inlet 312 having a gas inlet tube 314 fitted therein. The apparatus 300 also includes a gas outlet 316 having a gas outlet tube 318 fitted therein. The gas inlet 312 is adapted to allow a gas composition to be introduced into the gas cavity 310, while the gas outlet 316 is adapted to allow the gas composition to exit the gas cavity 310. The gas in the gas cavity 310 in conjunction with the gas permeable membrane to allow gas transport into and exchange with the zones 216. Of course, a similar design can be used for the chambers 240 and 270 of FIGS. 2E&F, respectively. Additionally, the gas cavity 310 can be physically partitioned so that a different gas composition can be supplied to each zone, such a partitioning would, of course, require additional gas inlets and outlets as shown in FIG. 3C.

Figure 4A:
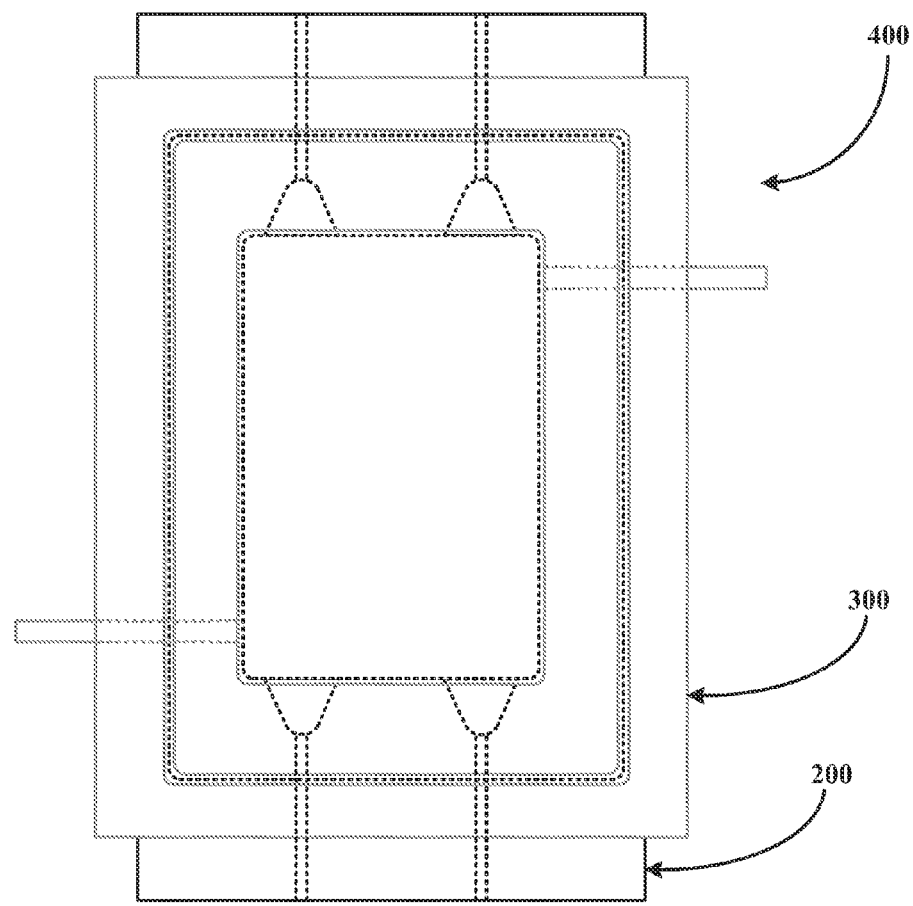
FIG. 4A depicts an assembly of the laminar flow cell culture chamber of FIGS. 2A&B and the gas chamber of FIGS. 3A&B.
Figure 4B:
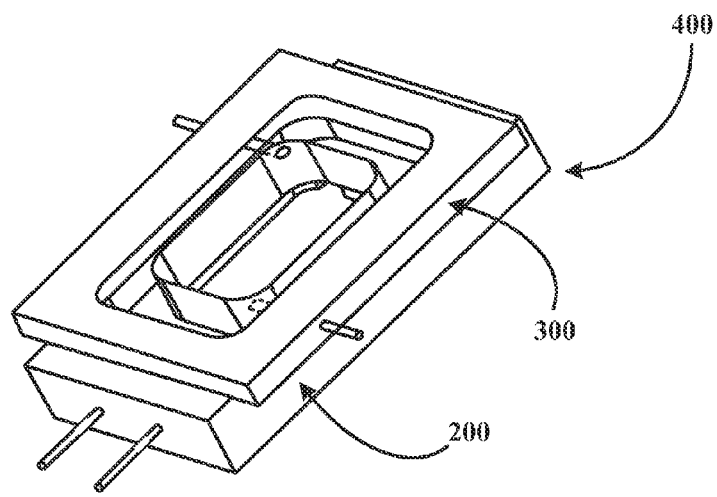
FIG. 4B depicts a 3D rendering of the assembly of FIG. 4A.

Referring now to FIGS. 4A&B, a plan view and 3D perspective view of a combined apparatus of this invention, generally 400, is shown to include the chamber 200 and the gas chamber 300 properly attached. The chamber 200 is shown in black line and the gas chamber 300 is shown in grey line.

Figure 5A:
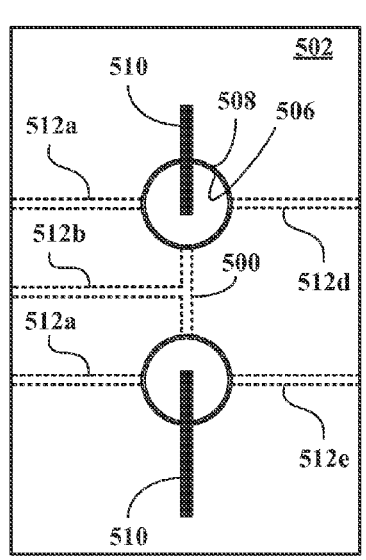
FIGS. 5A-C depict a top, front, and side views of an embodiment of an inlet valve of this invention.
Figure 5C:
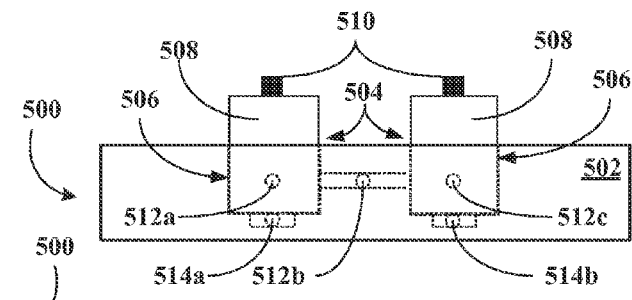
Figure 5B:
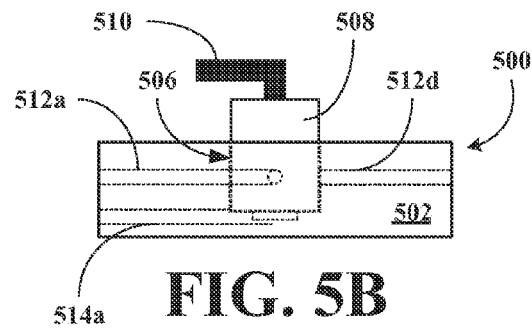
Figure 5D:
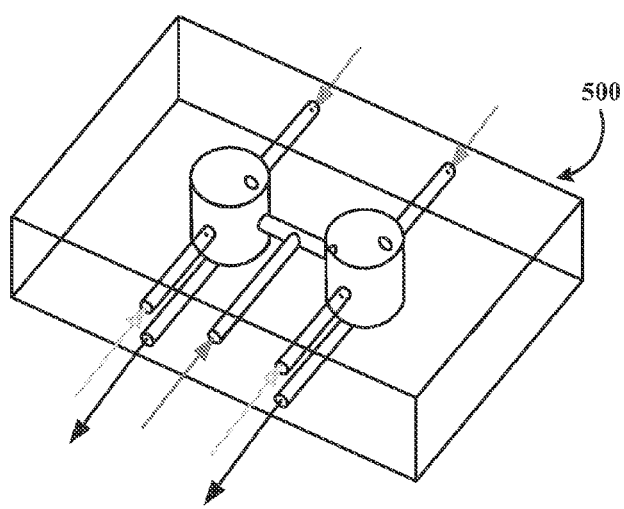
FIG. 5D depicts a 3D rendering of the inlet valve of FIGS. 5A-C showing flow paths.
Figure 6A:
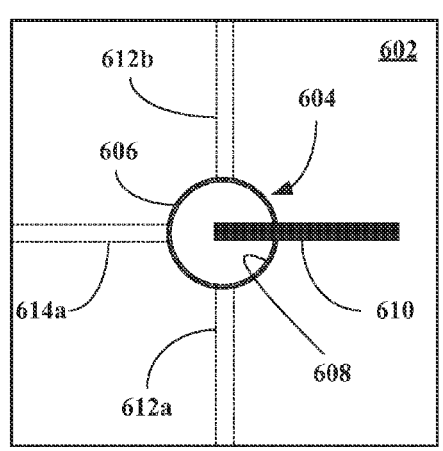
FIGS. 6A-C depict a top, front, and side views of an embodiment of an outlet valve of the invention.
Figure 6C:
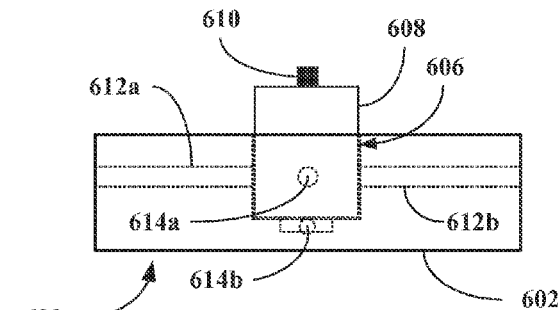
Figure 6B:
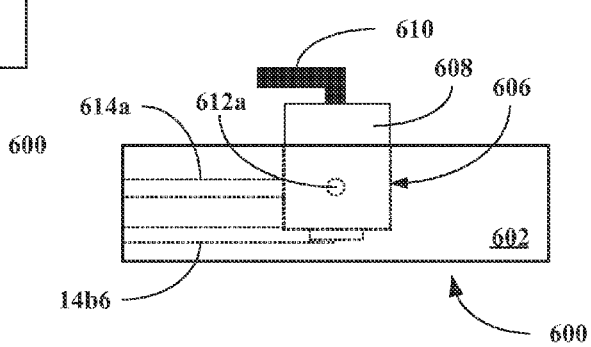
Figure 6D:
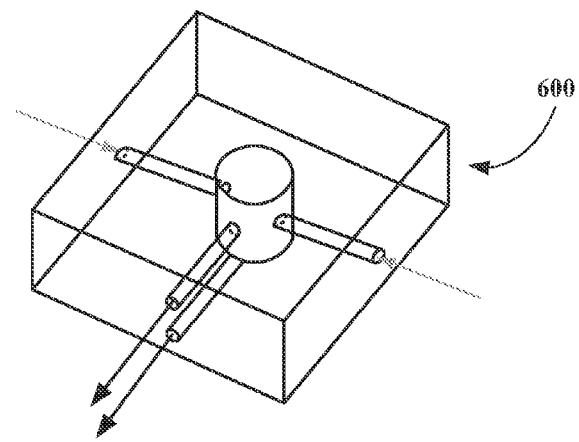
FIG. 6D depicts a 3D rendering of the outlet valve of FIGS. 6A-C showing flow paths.

Referring now to FIGS. 5A-C, an embodiment of an inlet valve apparatus of this invention, generally 500, is shown to include a body 502. The body 502 includes two valves 504. Each valve 504 includes a cylindrical cavity 506 adapted to receive a rotatable valve barrel 508 having a handle 510. The apparatus 500 also includes five inlets 512*a-e*, all of which can be equipped with inlet tubes (not shown). The inlets 512*a-e* are adapted to be connected with reservoirs or to support medium recycling. The apparatus 500 also includes two outlets 514*a-b* adapted to be connected to the inlets of the zone 216 of the chamber 200 of FIG. 2A. All of the inlets 512*a-e* and the outlets 514*a-b* open into their respective cylindrical cavities 506. The barrels 508 include flow paths permitting different inlets to be connected to the outlets to control the medium composition being supplied to each zone. Thus, each valve 504 can be used to combine up to three flow together to form the outlet flow. Looking at FIG. 5D, a perspective 3D rendering of the valve 500 is shown. The arrows indicate the flow directions associated with the inlets 512*a-e* and outlet 514*a-b*. The 3D rendering shows an inlet on the right side of the right valve, which represent an error in the rendering. However, each valve 504 can include additional inlets and outlets, but the barrel configuration and construction becomes more challenging.

Referring now to FIGS. 6A-D, an embodiment of an outlet apparatus of this invention, generally 600, is shown to include a body 602. The body 602 includes a valve 604. The valve 604 includes a cylindrical cavity 606 adapted to receive a rotatable valve barrel 608 having a handle 610. The apparatus 600 also includes two inlets 612, all of which can be equipped with inlet tubes (not shown). The inlets 612 are adapted to be connected with the chamber outlet tubes 228. The apparatus 600 also includes two outlets 614 adapted to be connected to the a sample collection container or to a waste bag as shown in FIG. 1A. All of the inlets 612 and the outlets 614 open into the cylindrical cavity 606. The barrel 608 includes flow paths permitting the inlets to be connected to wither one of the outlets to control the chamber effluent to either the sample collection container or the waste bag. Of course, the outlet value 600 can include additional outlets for directly spent medium to the inlet valve 500 for re-circulation to the chamber 200.

Figure 7:
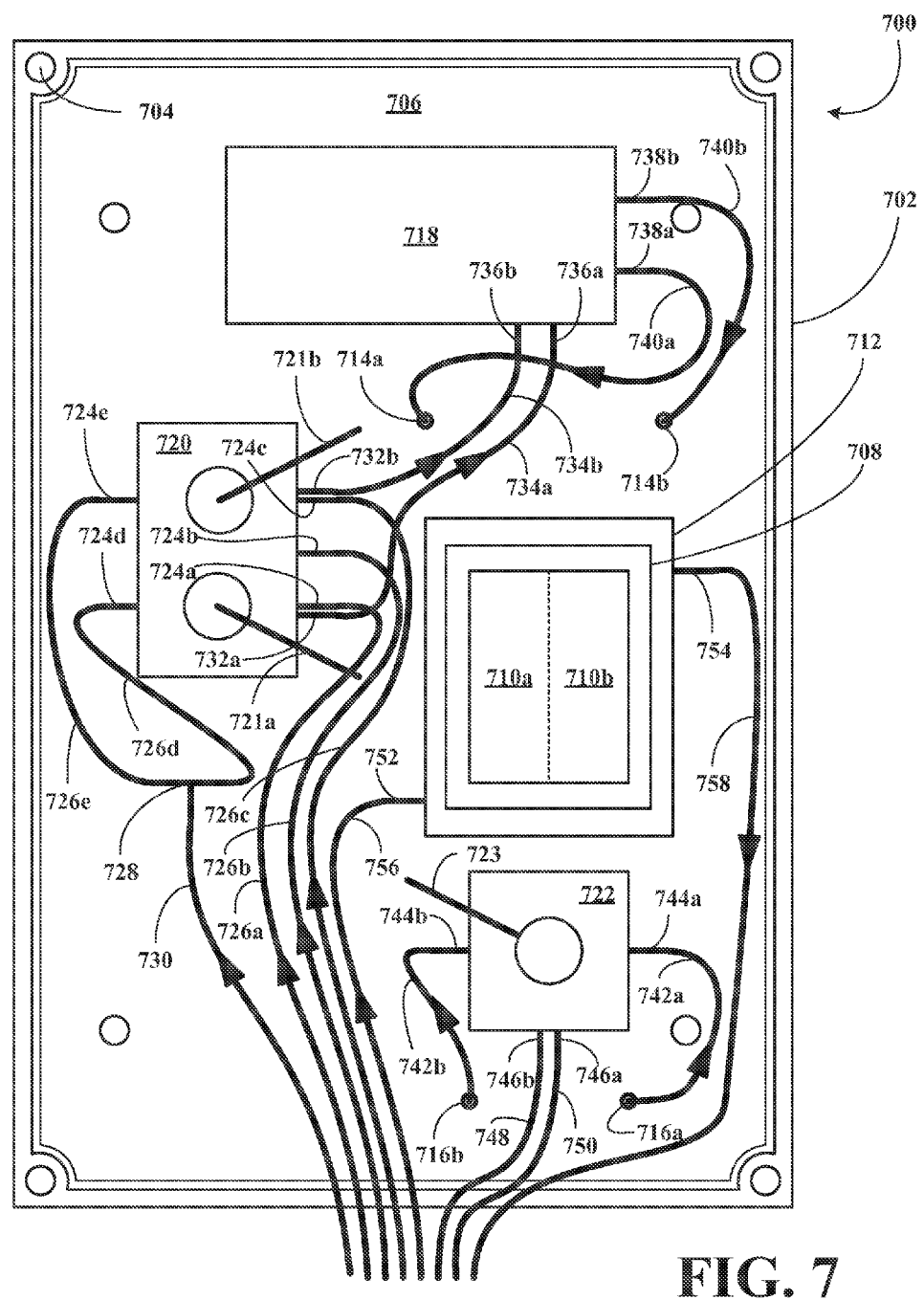
FIG. 7 depicts an embodiment of a bioreactor apparatus of this invention including the assembly of FIG. 4A.

Referring now to FIG. 7, an embodiment a bioreactor of this invention, generally 700, is shown to include a housing 702 having four corner apertures 704 adapted to receive a cover (not shown). The housing 702 includes a bottom mounting member 706 upon which other components are mounted and below which certain tubing leading to certain components run. Mounted on the member 706 is a laminar flow chamber 708 of FIG. 2A having two laminar flow zones 710*a&b* The chamber 708 are equipped with a gas chamber 712. The inlets and outlets of the chamber 708 (not shown) are connected to tubes running under the mounting member 706. The inlet tubes terminate in two tube inlets 714*a&b*, and the outlet tubes terminate in two tube outlets 716*a&b*. The apparatus 700 also includes a pump 718, an inlet valve 720, and an outlet valve 722 all mounted on the mounting member 706. The apparatus 700 also include conduits connecting the components. In this configuration, the inlet valve 720 includes five inlets 724*a-e*. The inlet 724*a* is connected to a first reservoir not shown via a conduit 726*a*; the inlet 724*b* is connected to a second reservoir not shown via a conduit 726*b*, the inlet 724*c* is connected to a second reservoir not shown via a conduit 726*c*, and the inlets 724*d&e* are connected via T conduits 726*d&e* from a T connector 728, which is connected to a medium re-circulation conduit 730. The inlet valve 720 also includes two outlets 732*a&b* connected to via pump inlet conduits 734*a&b* to pump inlets 736*a&b* of the pump 718. The inlet valve 720 includes valve selection handles 721*a&b*, which control the fluid in and out of the valve 720. The pump 718 also includes pump outlets 738*a&b* which are connected via pump outlet conduits 740*a&b* to the tube inlets 714*a&b* for supplying medium to the zones 710*a&b*. The tube outlets 716*a&b* for removing spent medium from the zones 710*a&b* are connected via outlet valve inlet conduits 742*a&b* to outlet valve inlets 744*a&b* of the outlet valve 722. The outlet valve 722 has two outlets 746*a&b*. In this configuration, the outlet valve 722 has two settings for directing spent medium controlled by an outlet valve handle 723. The spent medium can be directed via a waste collection conduit 748 to a waste container or bag (not shown). Alternatively, the spent medium can be direct via a sampling/recycling conduit 750 to either a sample collection container or to the re-circulation conduit 730. The gas chamber 712 include a gas inlet 752 and a gas outlet 754. The gas inlet 752 is connected via a gas inlet conduit 756 to a gas handling system (not shown) adapted to supply the gas chamber 712 with a gas composition to support gas transport and exchange with the zones 710*a&b*. The gas outlet 754 is connected via a gas outlet conduit 758 to a gas disposal system or vent (not shown), depending on the nature of the gas composition being supplied to the chamber 712.

Figure 8:
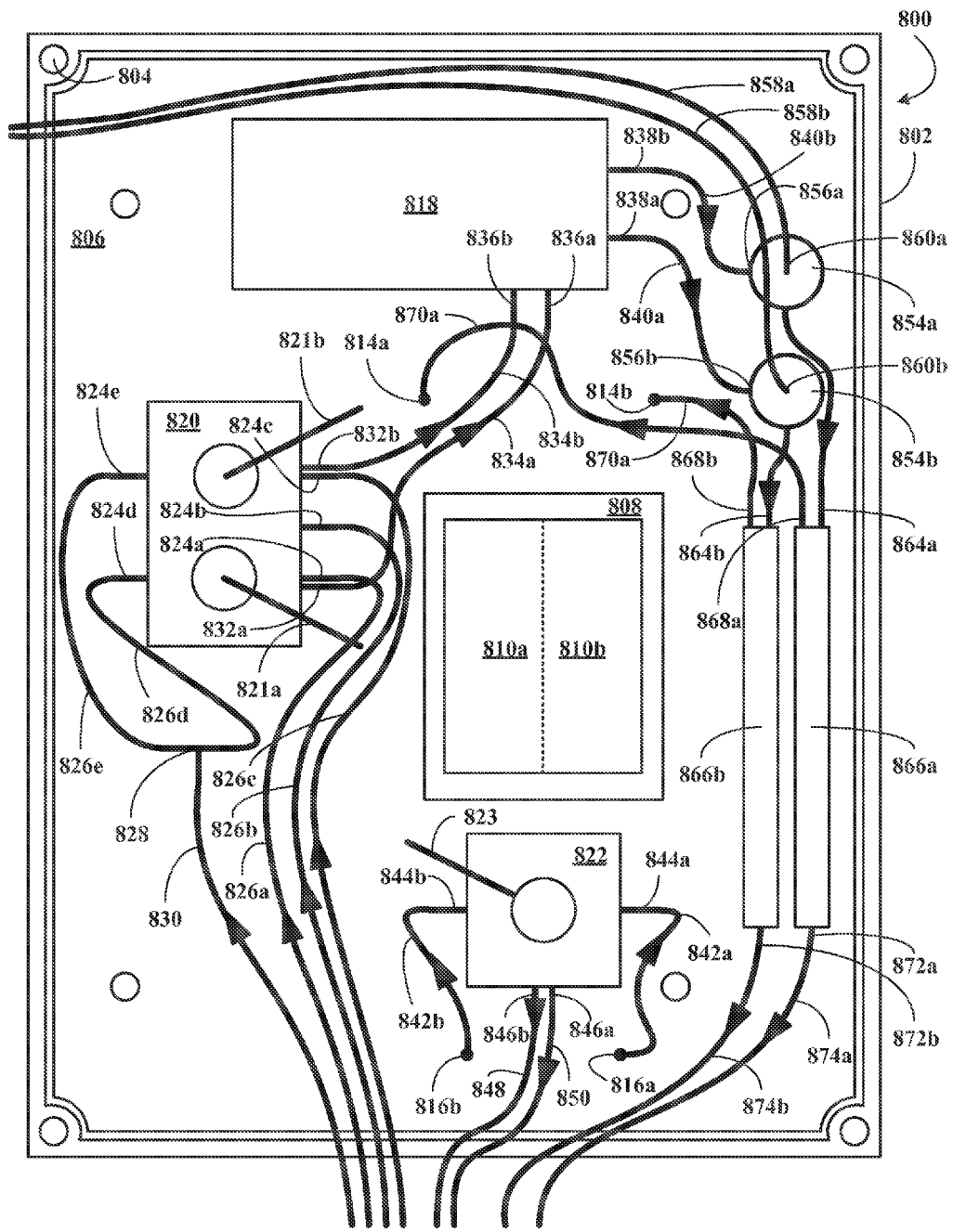
FIG. 8 depicts another embodiment of a bioreactor apparatus of this invention including a inline medium gasification assembly.

Referring now to FIG. 8, another embodiment of a bioreactor of this invention, generally 800, is shown to include a housing 802 having four corner apertures 804 adapted to receive a cover. The housing 702 includes a bottom mounting member 806 upon which other components are mounted and below which certain tubing leading to certain components run. Mounted on the member 806 is a laminar flow chamber 808 of FIG. 2A having two laminar flow zones 810*a&b*. The inlets and outlets of the chamber 808 (not shown) are connected to tubes running under the mounting member 806. The inlet tubes terminate in two tube inlets 814*a&b*, and the outlet tubes terminate in two tube outlets 816*a&b*. The apparatus 800 also includes a pump 818, an inlet valve 820, and an outlet valve 822 all mounted on the mounting member 806. The apparatus 800 also include conduits connecting the components. In this configuration, the inlet valve 820 includes five inlets 824*a-e*. The inlet 824*a* is connected to a first reservoir not shown via a conduit 826*a*; the inlet 824*b* is connected to a second reservoir not shown via a conduit 826*b*, the inlet 824*c* is connected to a second reservoir not shown via a conduit 826*c*, and the inlets 824*d&e* are connected via T conduits 826*d&e* from a T connector 828, which is connected to a medium re-circulation conduit 830. The inlet valve 820 also includes two outlets 832*a&b* connected to via pump inlet conduits 834*a&b* to pump inlets 836*a&b* of the pump 818. The pump 818 also includes pump outlets 838*a&b* which are connected via pump outlet conduits 840*a&b*. The tube outlets 816*a&b* for removing spent medium from the zones 810*a&b* are connected via outlet valve inlet conduits 842*a&b* to inlets 844*a&b* of the outlet valve 822. The outlet valve 822 has two outlets 846*a&b*. In this configuration, the outlet valve 822 has two settings for directing spent medium. The spent medium can be directed via a waste collection conduit 848 to a waste container or bag (not shown). Alternatively, the spent medium can be direct via a sampling/recycling conduit 850 to either a sample collection container or to the re-circulation conduit 830.

In this configuration, the bioreactor 800 does not include a gas chamber, but instead includes a gas infusion system 852. The gas infusion system 852 is adapted to introduce gas into the medium downstream of the pump 818 and upstream of the tube inlets 814*a&b*. The system 852 includes two bubble traps 854*a&b* connected via pump outlet conduits 840*a&b* to bubble traps medium inlets 856*a&b*. The bubble traps 854*a&b* are connected via gas supply conduits 858*a&b* to a gas supply (not shown), where each gas supply conduit 858*a&b* generally includes gas regulator valve (not shown) to control the rate of gas supplied to the traps 854*a&b*. The bubble traps 854*a&b* are adapted to supersaturate the medium with a gas composition. The gasified medium then exits the bubble traps 854*a&b* through bubble trap outlets 860*a&b*, which are connected via bubble trap outlet conduits 862*a&b* to gasified medium inlets 864*a&b* of two gas exchangers 866*a&b*. The gas exchangers 868*a&b* include gas exchanged medium outlets 868*a&b*, which are connected via gas exchanged medium conduits 870a&b to the tube inlets 814a&b of the zones 810a&b. The gas exchangers 866a&b also include gas outlets 872a&b connected via gas outlet conduits 874a&b to gas vents (not shown). The gas exchangers 866a&b provide for gas exchange in the medium so that the medium includes a desired concentration of the gas composition introduced into the medium by the bubble trap 854a&b. The system 852 is adapted to supply the zones 810a&b with a medium including an amount of a dissolved gas composition to achieve a desired affect. The gas composition can be designed to support cell growth or subject the cells in the zones to adverse conditions to monitor cell response. The gas composition can be changed and agents introduced into the medium to test drugs or other gas compositions to test and monitor cell response and recovery.

Methods Using the Bioreactors of this Invention

Generally, the methods of the present invention for short, moderate or long term cell cultures using the apparatuses 700 or 800 described above, include the step of isolating cells (either prokaryotic or eukaryotic). After isolation, the cells are then inoculated into zones of the laminar flow cell culture chamber 200, 240 or 270 using a culture medium, where the chamber can be sterilized. The cells are then allowed to proliferate to desired cell density for suspension cell lines or to a confluent monolayer for adherent cell lines. If desired, cells are treated with a label or other tag such as a fluorescent cell probe. Once a desired population is attained, the cells are harvested by manipulating fluid dynamics to achieve cell removal from one or all zones of the chamber. The harvesting can include removing spent media, washing with saline, and treating with protease to break protein anchorages. The method can also include the step of accumulating waste in a waste bag. Harvested cells are collected. The collected cells can then be sent to an analytical system for additional analysis. For longer cell cultures, harvesting is allowed to continue to a population so that the remaining cells in the harvested zone can migrate into the harvested area, and re-grow in the harvested area. Harvesting can be repeated whenever the cell population reaches a desired population. In this way, cell cultures can be maintained for long periods of time for long term cultures.

For chemotaxis studies, the method can include the step of adding different chemical agents to the culture medium during cell migration and observing the migration with the aid of a microscope to determine the effects of the chemical agent on cell migration and proliferation. For apoptosis studies, the method can include the step of adding known drugs to the culture medium and observing cell death rate with the aid of a microscope or external micro-analytical system. For mechanotaxis studies, the method can include the step of adjusting a shear level or shear gradient using different flow rates for different inlets and observing cell migration and/or proliferation with the aid of a microscope.

Figure 9A:
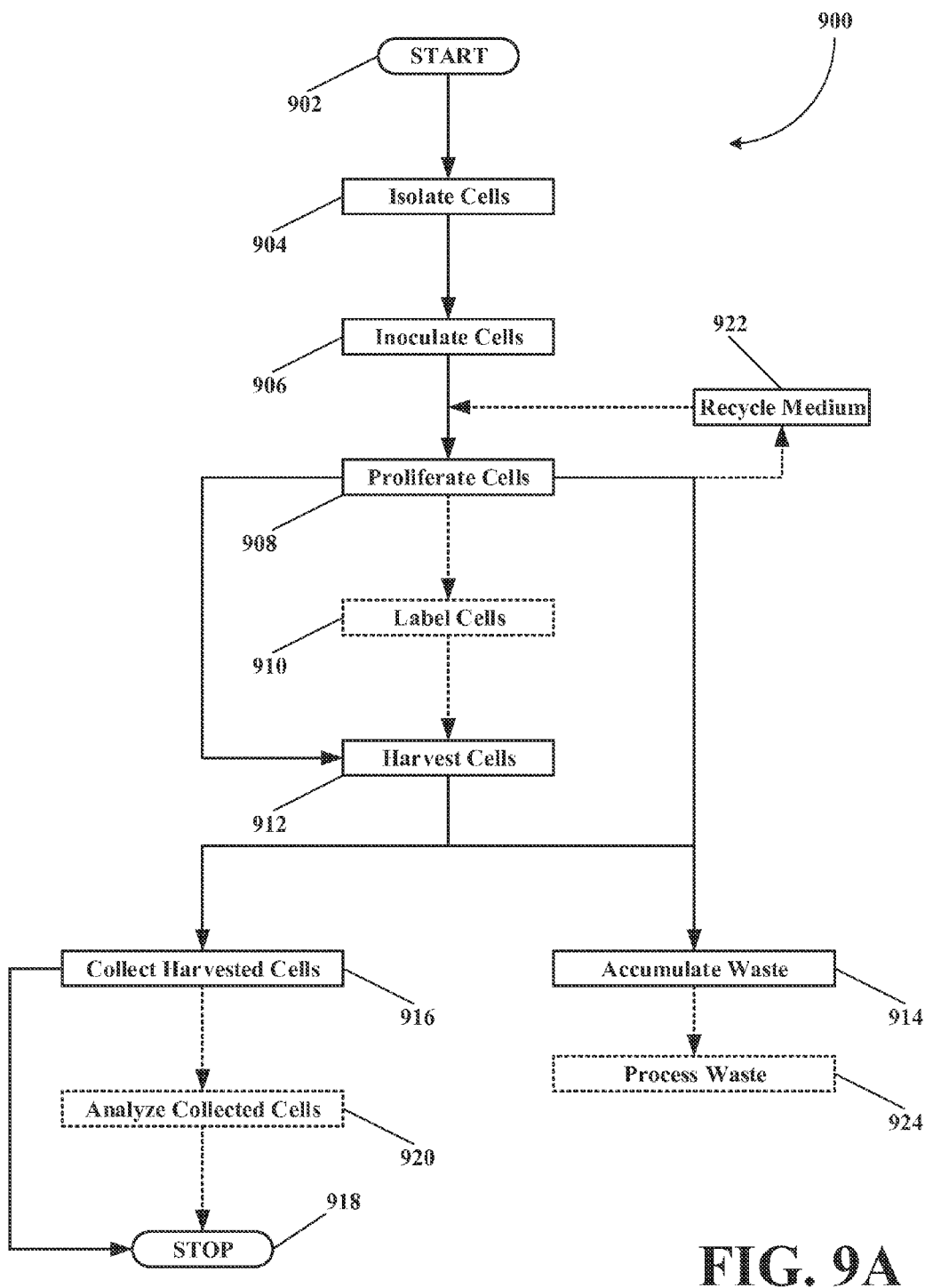
FIG. 9A depicts a flow diagram of an embodiment of a method for using the bioreactor of this invention for short term cultures and studies.

Referring now to FIG. 9A, an embodiment of a method of this invention, generally 900, is shown to include a start step 902, which is merely to evidence a start in an culture study. The start step 902 would generally include all the preparatory work necessary to perform a cell cultures study using the laminar flow cell culture chamber 200, 240 or 270 described above. After everything is ready, the method includes the step of isolating cells for culturing in an isolate cells step 904. The isolated cells are mixed with medium and introduced into one or all of the zones of a laminar flow chamber of this invention in an inoculate cells step 906. After inoculation, medium flow is adjusted to support a laminar flow of medium to support cell growth in the zones in a proliferate cells step 908. Once a desired population of cells has been reached in a zone, the method can optionally include a label cells step 910, where a cell label is introduced into the medium to label the cells prior to harvesting the cell population in a harvest cells step 912. Alternatively, once the desired cell population is achieved, the cell population can be harvested directly in the harvest cells step 912. During cell proliferation, spent medium is forwarded to a waste container in an accumulate waste step 914. After cell harvesting, medium is separated from the harvested cells and forwarded to the waste container. The harvested cells are then collected in a collect harvested cells step 916. After collecting the harvested cells, the cells can be stored stopping the study in a stop step 918. Alternatively, the collected cells can be forwarded to a cell analysis system in an analyze collected cells step 920. The method 900 can also optionally include the step of recycling spent medium in a recycle medium step 922. The method 900 can also include processing waste or spent medium to extract cell products, if the cells are secretory cells in a process waste step 924.

Figure 9B:
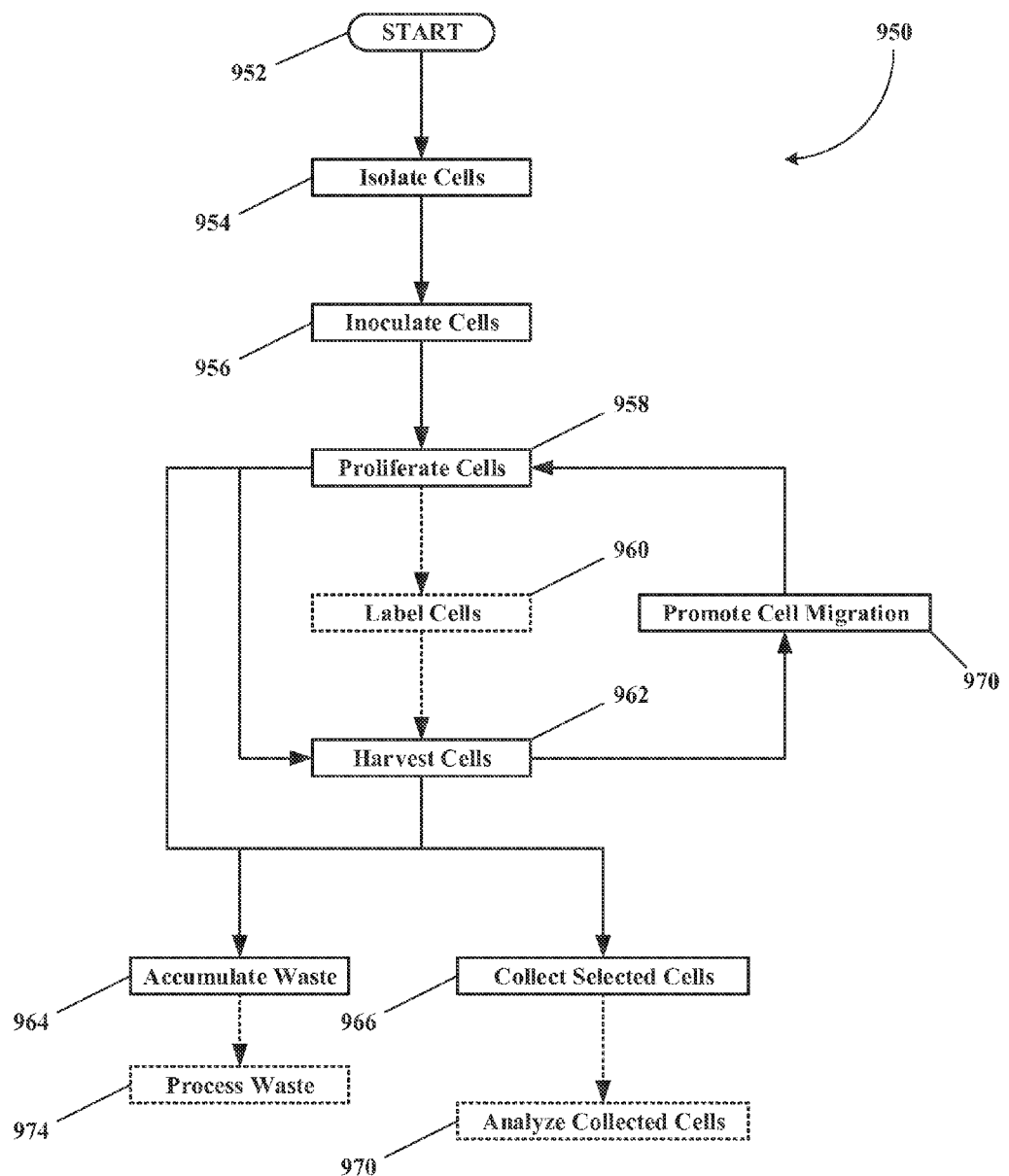
FIG. 9B depicts a flow diagram of an embodiment of a method for using the bioreactor of this invention for moderate and long term studies.

Referring now to FIG. 9B, an embodiment of a method of this invention, generally 950, is shown to include a start step 952, which is merely to evidence a start in an culture study. The start step 902 would generally include all the preparatory work necessary to perform a cell cultures study using the laminar flow cell culture chamber 200, 240 or 270 described above. After everything is ready, the method includes the step of isolating cells for culturing in an isolate cells step 954. The isolated cells are mixed with medium and introduced into one or all of the zones of a laminar flow chamber of this invention in an inoculate cells step 956. After inoculation, medium flow is adjusted to support a laminar flow of medium to support cell growth in the zones in a proliferate cells step 958. Once a desired population of cells has been reached in a zone, the method can optionally include a label cells step 960, where a cell label is introduced into the medium to label the cells prior to harvesting the cell population in a harvest cells step 962. Alternatively, once the desired cell population is achieved, the cell population can be harvested directly in the harvest cells step 962. During cell proliferation, spent medium is forwarded to a waste container in an accumulate waste step 964. After cell harvesting, medium is separated from the harvested cells and forwarded to the waste container. The harvested cells are then collected in a collect harvested cells step 966. Alternatively, the collected cells can be forwarded to a cell analysis system in an analyze collected cells step 970. The method 950 can also optionally include the step of recycling spent medium in a recycle medium step as in the method 900 above (not shown). The method 950 can also include processing waste or spent medium to extract cell products, if the cells are secretory cells in a process waste step 974. The method 950 is designed for moderate to long term cultures studies, where a cell population is allowed to grow to a given density harvested to a relatively low population so that the remaining cells can migrate and re-populated the harvested zone. This process is repeated as long as the remaining cells are capable of re-populating the zone. Thus, the method 950 includes a promote cell migration step 976 permitting moderate and long term culture studies.

Bioreactor Characteristics and Properties

As stated in the priority document, the laminar flow cell culture apparatus of this invention includes a laminar flow cell culture chamber as shown in FIGS. 2A-F. The chamber has disposed on its top a controlled gas chamber as shown in FIG. 3A-4B. Once assembled, the culture chamber is are separated from the controlled gas chamber by a gas permeable membrane.

The laminar flow cell culture chamber is built to allow laminar flow of fluids. Fluids (not shown) injected through conduits connected to the culture chamber inlets provide flow in a parallel direction (no mixing) through the culture chamber and exit via the culture chamber outlets through exit conduits subsequent handling and/or processing. The culture chamber does not required a physical barrier such as a membrane to separate flows in the laminar flow zones within the chamber. The distance that separates the laminar flows is typically about 2 mm, but the separation can be more of less depending on design consideration and the degree zone interaction is desired. In another configuration as shown in FIGS. 2E&F, the laminar flow cell culture chamber can handle more than two laminar flow regions. Such configurations allow co-culture of two or more than two batches of cells, simultaneously. The flow isolation also permits each region or zone to be include different medium so that signaling between flow regions are be studied.

In miniature embodiment, the culture laminar flow cell culture chamber has a volume of one mL or less. In most embodiments, the laminar flow cell culture chamber includes a substrate conducive to cell growth forming an interior surface of the chamber. Such substrates are typically made of a polystyrene matrix, but any cell conducive substrate can be used as well.

In most embodiments, the laminar flow cell culture chamber is sealable and sterilized to provide cells with optimum growth conditions. In most embodiments, the outer walls of the laminar flow cell culture chamber are made of optically transparent biocompatible materials such as glass or polystyrene. Optically transparent walls provide a window for direct observation of cells through a detection apparatus such as a light microscope or other optical detection device.

The laminar flow cell culture chamber is connected to the other components of the bioreactor via conduits or tubing that connects the inlets and outlets of the chamber to inlet and outlet control valves. The inlet and outlet valves are provided for transferring materials into and out of the zones of the laminar flow cell culture chamber.

Details of the laminar flow cell culture chamber are illustrated in FIGS. 2A-D. In this configuration, the chamber has two ingoing connections and two outgoing connections. However, in the configurations of FIGS. 2E-F, the chamber has more than two connections in and out. In some embodiments, especially for miniature embodiments, the chamber has inside dimensions of about 0.8 inch long by about 0.6 inch wide and about 0.06 inch thick. Dimensions used in these descriptions are meant by way of example and are not meant to limit the scope of the invention.

Details of the controlled gas chamber are shown in FIGS. 3A&B. The gas chamber is adapted to allow a controlled gas composition, flow and pressure into the gas chamber so that gas can be transferred into and exchanged with the zones via the gas permeable membrane, such as, but not limited to, a polystyrene gas permeable member. In some embodiments, especially for miniature embodiments, the gas chamber has dimensions of about 0.8 inch long, about 0.6 inch wide and about 0.22 inch thick. The controlled gas chamber has gas connections to a gas handling system to allow the passing of gas through the gas chamber.

Details of an embodiment of an inlet valve for use in this invention is shown in FIGS. 5A-D, while details of an embodiment of an outlet valve for use in this invention is shown in FIGS. 6A-D. The valves can be under computer control for automatic control of the opening and closing of the valves, allowing automated and unmanned operation of the bioreactor. Although the inventors constructed valves especially for the bioreactors of this invention, it should be recognized that any valve or series of valves can be used to facilitate the introduction and removal of medium into and out of the zones of the culture chamber.

FIGS. 7&8 illustrate embodiments of a bioreactor of this invention including a cultures chamber, inlet valve, outlet valve and a fluid handling system mounted on a mounting member of a housing. FIGS. 1A&B illustrate flow diagrams depicting flow pathways for two illustrative embodiments of a bioreactor of this invention. In the flow diagram of FIG. 1A, three fluid reservoirs (e.g., medium, Trypsin/EDTA, PBS) are connected to an inlet selection valve. The inlet selection valve is in turn connected to a miniature peristaltic pump (Instech™ OEM P625), which supplies medium to the zone inlet of each zone of the chamber. The zone outlets are connected to an outlet selection valve. The outlet selection valve is connected to a sample reservoir and a waste bag, and the flow from the zones are directed to either the sample reservoir or the waste bag as required by the operator or the computer software.

Fluid dynamic manipulations are used to provide control over the cell culture environment within the device including medium infusion, selective cell removal, and establishment of chemical gradient and/or physical gradient. The inlet selection-valve permits different combinations of fluid reagents to enter the inlet ports of the zones of the culture chamber, while a outlet selection-valve guides the exiting fluid to a waste bag or sample reservoir. The pressure driven flow inside the zones of the culture chamber is controlled via a miniature peristaltic pump. Gas exchange is achieved via a gas permeable membrane between the culture chamber and a gas chamber disposed above the membrane. Temperature is maintained externally with a Peltier element and a PID controller. Glass windows are strategically placed to enable phase-contrast and fluorescent morphological studies using inverted microscopes. Protocols for the bioreactor processes are described herein.

Characterization of the Bioreactor Flow Regime

Characterization of the hydrodynamic environment in bioreactors is essential for the evaluation of vessel performance. Proper fluidization, low shear stress, and adequate mass transport of nutrients are all characteristics of a well-designed culture chamber. A numerical model was developed in FLUENT™ to evaluate these critical parameters in the design of the cell culture chamber.

The three-dimensional bioreactor domain was discretized into a finite number of small control volumes using a commercial mesh generator, Gambit™. The computational fluid dynamics package, FLUENT™, was employed to compare analytical estimates. The fully developed, steady-state, laminar flow field in the bioreactor is found by solving the equations of conservation of mass and momentum. Numerical investigations were performed to evaluate the bioreactor's capability to perform selective cell removal, generate a chemical gradient, and evaluate fluid shear levels under typical working conditions.

Selective Cell Removal

Figure 10D:
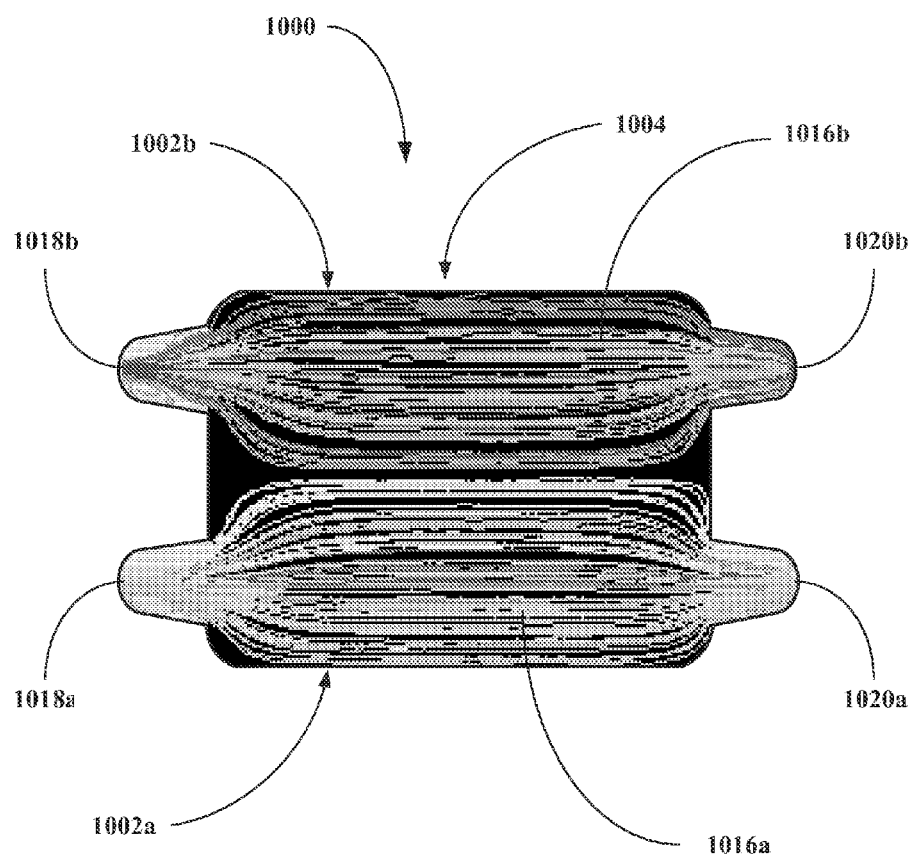
FIG. 10D depicts a simulation of flow lines or flow pathlines within the zones of a chamber of FIG. 2A, one set of lines representing medium and the over representing protease concentration for releasing anchorage dependent cells from the zones.

Referring now to FIG. 10A, a computer generated simulation 1000 of an initial flow of fluid into a zone 1002a of a two zone chamber 1004 such as the chamber 200 of FIG. 2A is shown, where the initial fluid front as fluid containing cells for seeding enters the zone 1002a, while zone 1002b is left unaffected. During the initial inoculation of the zone 1002a with cells 1006 (here adhesive cells), the cells 1006 and anchorage proteins 1008 are randomly distributed within the zone 1002a as shown in FIG. 10B. After proliferation, the cells 1006 for a monolayer 1010 attached to a conducive substrate 1012 in the chamber 1004 by a protein anchorage layer 1014 as shown in FIG. 10C.

because the flow rates required to sustain the miniature culture are small, the Reynolds number is very low and flow in the central channel or in each zone possesses classic Hele-Slaw flow characteristics. The flow in the zones 1002a&b of the chamber 1004 is essentially a two-dimensional laminar flow created by the thin channel and low fluid velocity conditions. Laminar flow is characterized by fluid traveling in layers, where each element travels smoothly along simple, well-defined paths. This characteristic is exploited in anchorage dependent cultures to harvest cells from specific regions 1002a or 1002b of the chamber 1004 for analysis without disturbing cell in the other regions. FIG. 10D illustrates this phenomenon by depicting computer generated pathlines 1016a&b of fluid flowing into, through and out of the two zones 1002a&b of the chamber 1004 (see also the chamber 200 of FIG. 2A) under normal working conditions. Cells suspended in the medium will also follow these fluid pathlines 1016a&b. This characteristic can also be exploited for selective treatment or co-culture inoculation for interface studies.

Once a desired cell population within the zone 1002a is achieved, the cell population is removed from the zone 1002a as illustrated in a simulation the miniature bioreactor as shown in FIG. 10D. A user-defined-scalar was defined in FLUENT™ to mimic the scalar transport of enzyme dissociation solution Trypsin/EDTA (Trypsin-ethylene-diamine tetraacetic acid). FIG. 10D can be used to illustrate the removal of cells from the area 1002a in the chamber 1004 growing on a glass slip at the base of the chamber 1004 (see FIG. 2B). The flow rates in both inlets 1018a&b and out off both outlets 1020a&b are identical ($M_1=M_2=1.166\times10^{-6}$ Kg/s). In FIG. 10D, the pathlines 1016a represent a defined scalar concentration value for Trypsin in the medium flowing in the zone 1002a, while the pathlines 1016b represent a defined scalar concentration value for medium flowing in the zone 1002b. As shown in FIG. 10D, medium infuses in the bottom inlet 1018a and travel along the pathlines 1016a towards the bottom outlet 1020a. If the top zone 1002b is also being harvested, then the Trypsin/EDTA will flow in a similar manner along the pathlines 1016b in the zone 1002b. After infusion, the pump would be switched off to allow time for the enzymatic dissociation to occur in the region 1002a (approximately 3-5 minutes). During this process, Trypsin cleaves anchorage proteins 1008, while EDTA encourages cells 1006 to round up and internalize any other anchorage proteins 1008. As the enzyme solution works, cells 1006 will dissociate from the growth substrate 1012 and become suspended in the media (the reverse of the process illustrated in FIGS. 10B&C). Upon subsequent infusion of fresh media, the cells 1006 will be harvested from the treated region 1002a. A selection valve on the outlet side of the chamber 1004 will direct the harvested cells to a sample port and the spent medium to a waste reservoir. Cycling of the above procedures between the upper 1002b and lower 1002a zones enables the use of the culture chamber 1004 for long term studies of anchorage dependent cells. Suspension cells may also be cultured in the same device and sampled and/or harvested periodically simply by the infusion of new media. Efforts are generally required to redistribute cells away from the outlet after harvesting for efficient re-population.

Generation of Chemical Gradients

Although designed for selective cell removal, the geometry of the miniature bioreactor chamber and the fluid handling system make it ideal to study the effects of a known chemoattractant on the cell migration (chemotaxis). To model the development of a chemical gradient, a second user-defined-scalar was defined in FLUENT™ to mimic the scalar transport of a common chemoattractant into and through the zones. The scalar profiles are identical to those depicted in FIG. 10D, if the scalar Trypsin is replaced by some known chemoattractant. If chemotaxis is positive, cells will crawl in the direction perpendicular to the flow of reagent. In these problems, the Schmidt number, $S_C=v/D$, may be used to characterize the ratio of momentum to mass diffusivity in the bioreactor, where v is the kinematic viscosity and D is the mass diffusivity. The Schmidt number for this case is large, $S_C\sim1000$, and hence the momentum diffusivity will be the prime driver for the distribution of the chemical constituent generating a steep gradient of the scalar normal to the centerline of the bioreactor as predicted by the numerical model.

Figure 11A:
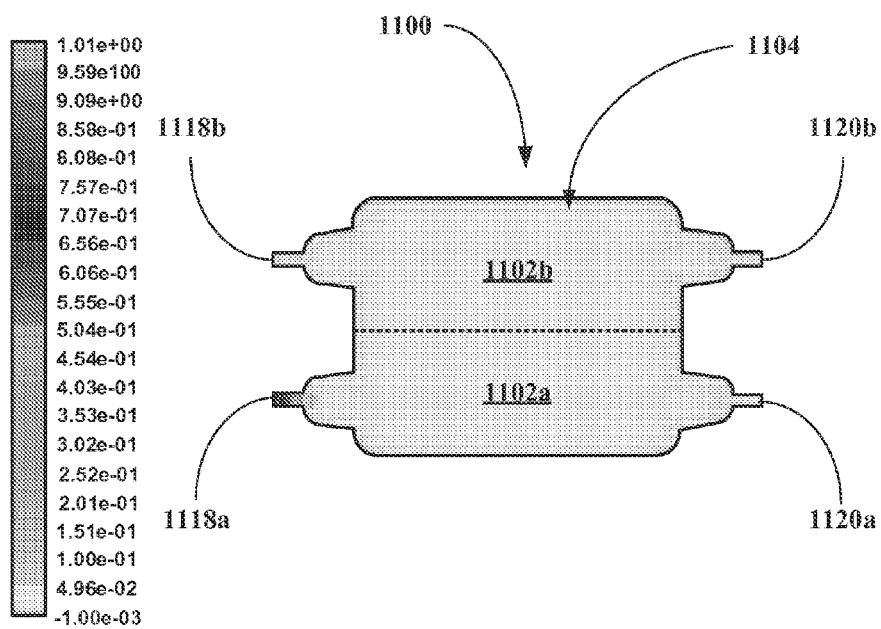
FIG. 11A-C depict a simulation sequence evidencing the establishment of a component gradient within a zone of a chamber of this invention.
Figure 11B:
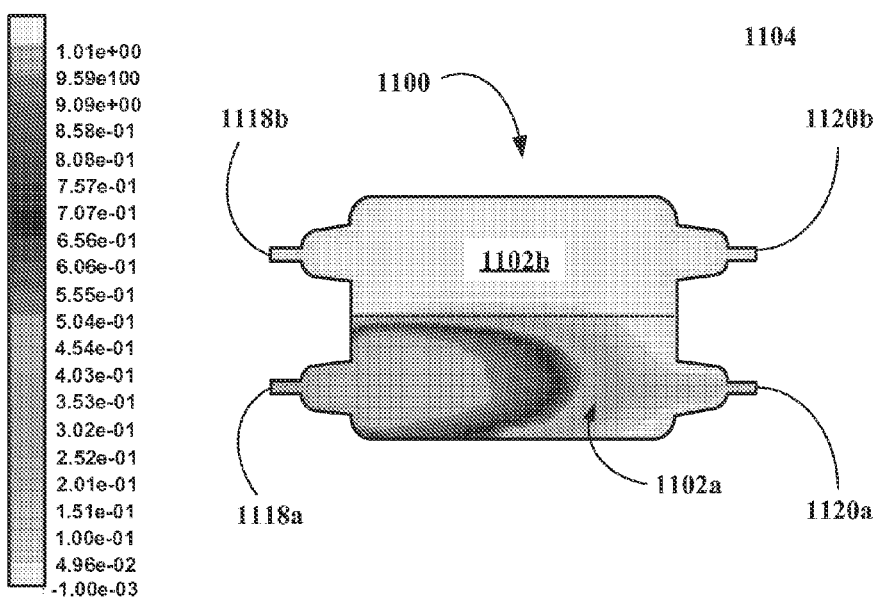
Figure 11C:
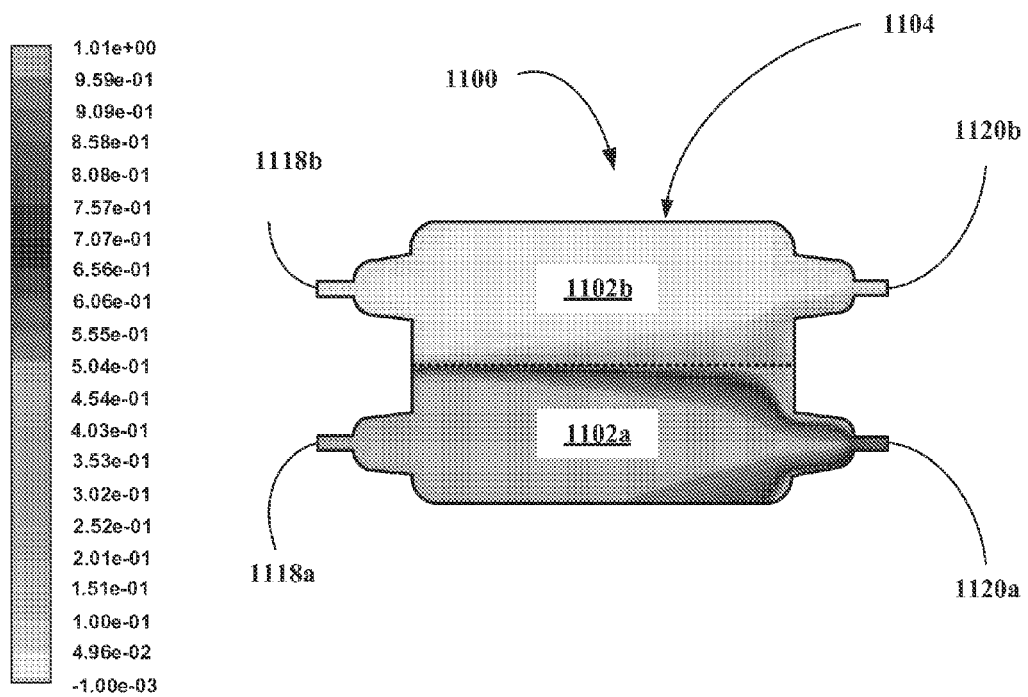

Referring now to FIG. 11A-C, simulations 1100a-c are designed to demonstrate selective cell removal and contours of a scalar transport in 1102a of a two zone chamber 1104 of a bioreactor apparatus of this invention. In FIG. 11A-C, the scalar transport is characterized by:

$Q_{TOT}$=0.14 mL/min.
$M_1=M_2=1.166\times10^{-6}$ Kg/s
scalar values between scalar_value$_1$=0 to scalar_value$_2$=1.

FIG. 11A shows the flow profile at t=1s; FIG. 11B shows the flow profile at t=150s; and FIG. 11C shows the flow profile as the profile hits the outlet 1120a.

Fluid Shear Levels

Quantifying shear stress levels in the zone 1100a is a significant element in evaluating the efficacy of the mammalian cell culture device and demonstrating its capabilities. Mammalian cells do not possess a cell wall; they are surrounded by a thin plasma membrane. As a result, they are highly sensitive to shear stresses imposed on them by their environment. Goodwin et al. (1993) [1] found that stress levels as low at 0.92 dynes/cm$^2$ adversely affected the growth of baby hamster kidney (BHK) cells. An estimate of the shear level can be obtained by assuming flow between parallel plates. The velocity profile is given by Equation (1):

$$\frac{u}{u_{max}} = \left(1-\left(\frac{2y}{h}\right)^2\right) \tag{1}$$

where u is the fluid velocity at some height y in the zone 1100a bioreactor, $u_{max}$ is the velocity along a centerline, and h is the gap or height in the chamber (~2 mm). The shear stress at the wall of the zone 1102a is given by Equation (2):

$$\tau = \mu\frac{du}{dy}\bigg|_{y/2} \tag{2}$$

where μ is the dynamic viscosity of the fluid media. Hence, fluid shear levels on a cell monolayer cultured in the zone 1102a can be approximated by Equation (3):

$$\tau = \frac{4\mu\cdot u_{max}}{h} = \frac{4\mu}{h}\left(\frac{3}{2}u_{avg}\right) = \frac{6\mu\cdot u_{avg}}{h} \tag{3}$$

Figure 12A:
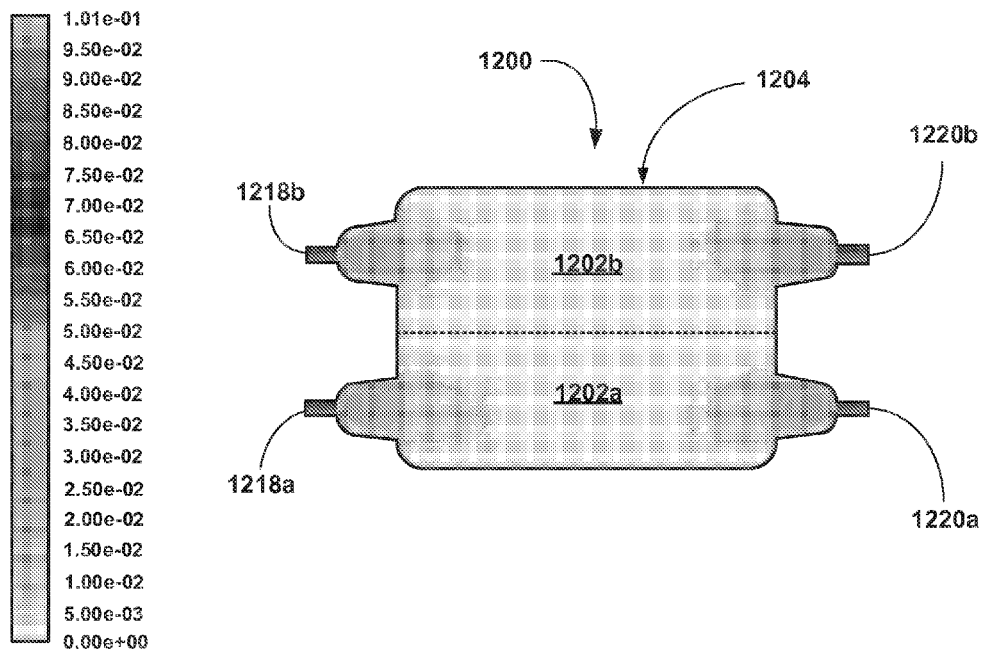
FIGS. 12A&B depict a simulation sequence evidencing wall shear stress levels produced within a chamber of this invention under normal working conditions.

This approximation was first acknowledged by Levesque and Nerem (1985) [2]. FIGS. 11A and 11B illustrate contours of wall shear stress under typical working conditions calculated by the numerical model described above. The contours in FIG. 12A illustrate that the shear levels are less than 0.005 dyne/cm$^2$ under normal operating conditions. The contours in FIG. 12B reveal slightly higher fluid shear levels (0.075 dyne/$cm^2$), but the flow rate is substantially higher (3.9 mL/min). These numerical findings correspond well with the analytical prediction above. Hence, the miniature bioreactor system can be used effectively as a low shear, fed batch culture device.

Figure 12B:
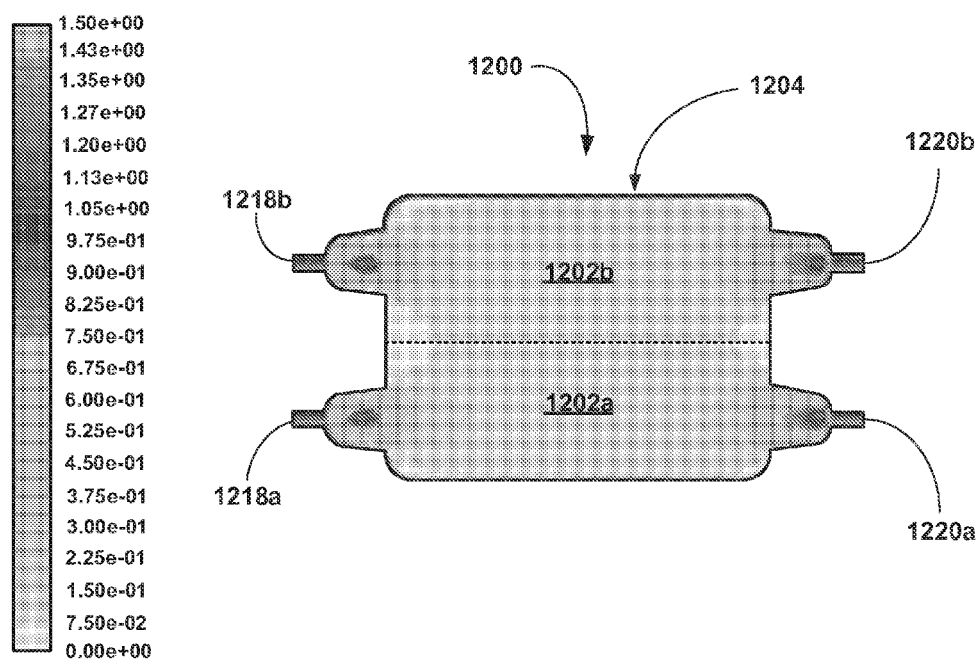

Referring now to FIGS. 12A&B, the contours of wall shear stress (dyne/$cm^2$). The greys colors are representative of wall shear stress levels (white low, grey intermediate). In FIG. 12A, the wall shear stress levels at $M_1=M_2=1.166\times10^{-6}$ Kg/s. Q=0.14 ml/min; and $\tau_{avg}$~0.005 dyne/$cm^2$. In FIG. 12B, the wall shear stress levels at $M_1=M_2=3.25\times10^{-5}$ Kg/s; Q=3.9 ml/min; and $\tau_{avg}$~0.075 dyne/$cm^2$.

Materials and Methods

Reagents and Solutions

Dulbecco's modified eagle's medium (DMEM; with 25 mM glucose and 4 mM glutamine), Hyclone fetal bovine serum (FBS), Sigma Trypsin-ethylene-diamine tetraacetic acid (EDTA), phosphate buffered saline (PBS), and Gibo penicillin-streptomycin solutions were all provided by (NASA/JSC). BHK-21 fibroblast culture medium for experiments consisted of DMEM supplemented with 10% (v/v) of FBS and 1% (v/v) penicillin-streptomycin.

BHK-21 Fibroblast Culture

BHK-21 cells were provided by NASA, JSC. The fibroblasts were cultured at 37° C. in a 25 $cm^2$ tissue culture flasks (Sigma-Aldrich) in a humidified atmosphere supplemented with 5% $CO_2$. Typically the cells were grown to confluence and passaged by trypsinization in 1× Trypsin-EDTA solution. The cell suspension was diluted 5:1 with fibroblast culture medium and centrifuged at 3000 rpm for 1 minute. After aspiration of the supernatant, the pellet was resuspended in fibroblast culture medium and approximately $1\times10^5$ or $5\times10^5$ cells were inoculated into each fresh bioreactor system depending on desired inoculation level.

Microchip Device

Figure 13:
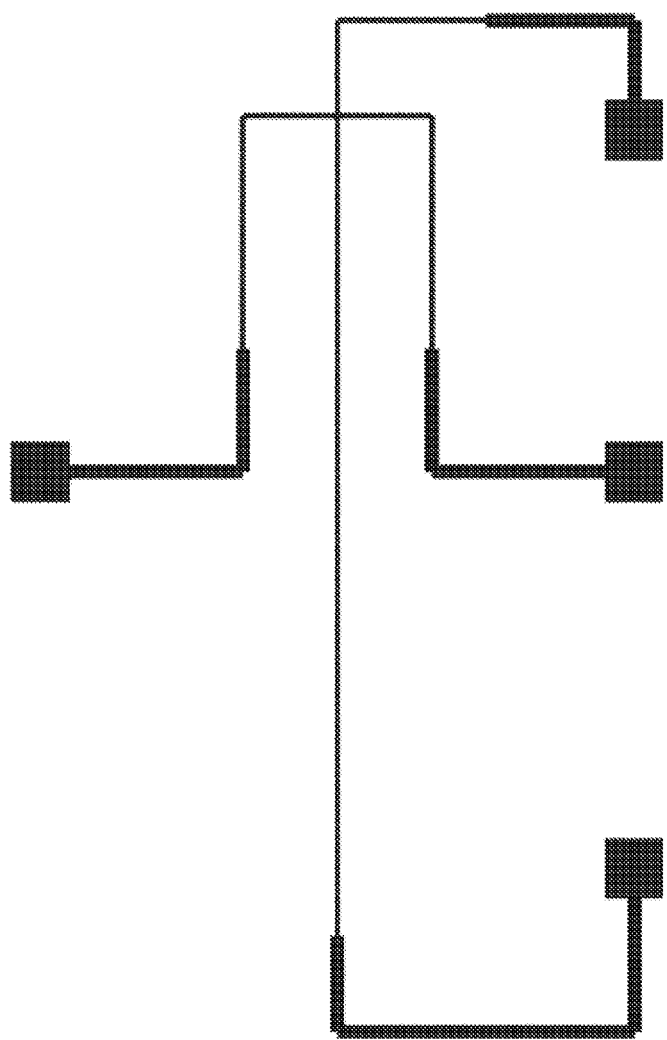
FIG. 13 depicts a schematic diagram of a microchip channel manifold for a cytometry microchip analyzer.

The bioreactor of this invention can be integrated into a micro-fluid apparatus such as a cytometry microchip. In such a configuration, an effluent from the bioreactor including harvested cells or cell products is forwarded to a cytometry microchip illustrated in FIG. 13. A glass microchips was fabricated at the Culbertson laboratory at KSU using standard photolithographic and wet chemical etching techniques previously described by Jacobson et al. 1994[3]. The channels on the microchip are 27 μm wide and 100 μm deep (flow through). All channel widths were measured at half-depth. Reservoirs were bonded to the chip via epoxy.

Microfluidics Cytometry Signal Detection

Harvested cells were fluorescently labeled with Calcein AM (Invitrogen, Molecular Probes, excitation/emission max ~494 & 517 nm) and detected as they pass through a blue (488 nm) solid state diode pumped crystal laser light beam. The laser light was focused on the channel in the microchip below the channel cross. Fluorescence emission was collected with a 40× objective and focused on an adjustable spatial filter. The signal was captured via a photomultiplier tube (PMT; 77348; Oriel) fashioned with an additional 1 mm spatial filter to reduce spurious noise.

EXPERIMENTS OF THE INVENTION

Miniature Bioreactor Preparation—Inoculation

The miniature bioreactor and fluid handling system was assembled in a biosaftey cabinet and rinsed with 70% isopropanol followed by a PBS/antibiotic flush (5% (v/v) penicillin-streptomycin). The entire system was then autoclaved at 80° C. for several hours. Supplemented DMEM, Trypsin/EDTA, and a PBS/antibiotic solution were introduced into the correct reservoirs. A second PBS/antibiotic flush was performed to ensure all the isopropanol was removed and the system was purged of air. DMEM was then infused into the bioreactor and the system was allowed to reach 37° C. Recently harvested cells were siphoned into a syringe. The syringe was attached to the inoculation port and its contents were injected slowly into the system as the pump was running to infuse cells into the bioreactor. Since the cells are typically cultured in media with the phenol red, cell inoculation was monitored colormetrically. The cells were allowed to attach to the growth surface before fresh media (with phenol red) was infused.

Results & Discussion

Figure 14A:
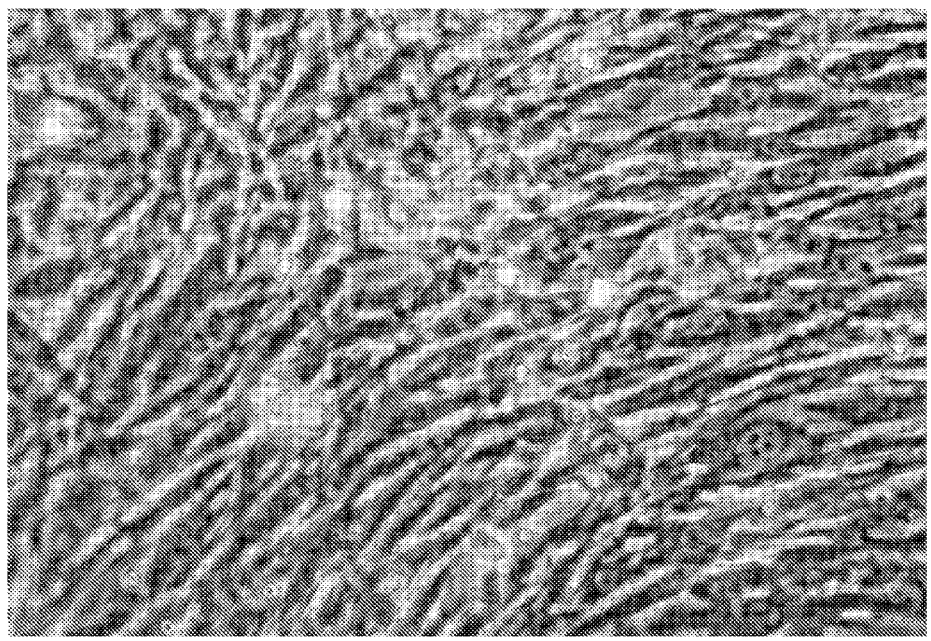
FIG. 14A is a photomicrograph of a confluent monolayer of BHK-21 cells in a zone of an chamber of FIG. 2A.
Figure 14B:
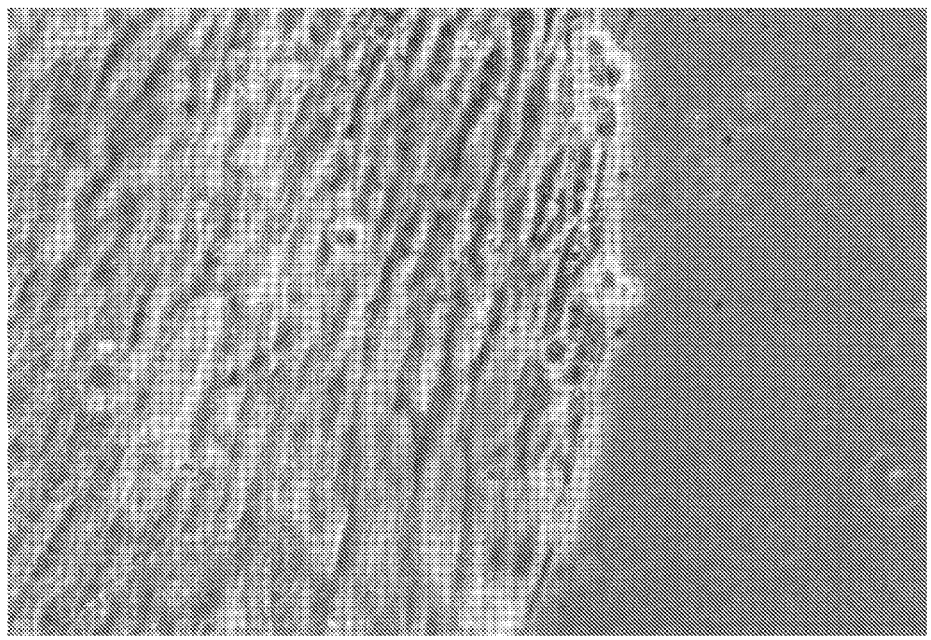
FIG. 14B depicts a photomicrograph of the zone after a selective harvesting of the cells in the zone.
Figure 15:
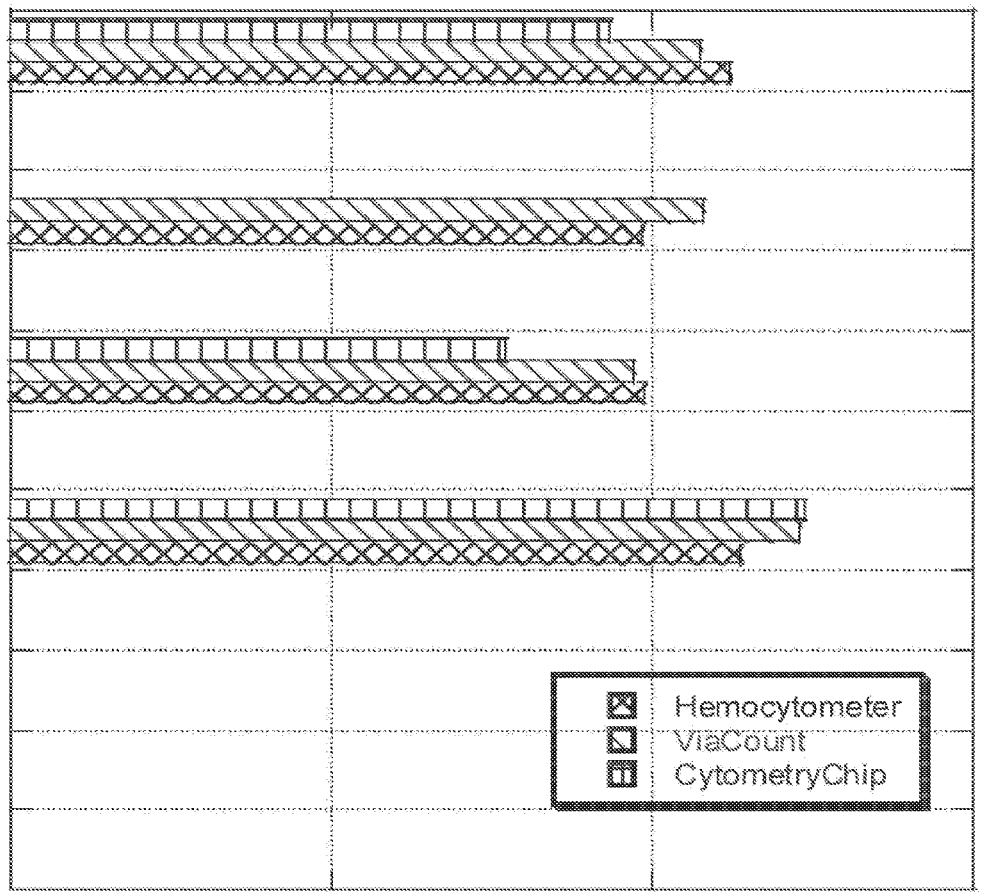
FIG. 15 depicts a cell number characterization study, where cell counts were determined via hemocytometer, Via-Count, and microchip cytometry single point analysis of FIG. 13.

Once cells reached desired confluence, cell harvesting protocols described above were initiated. One half of the culture was washed with a saline solution and then treated with an enzyme solution for dissociation from the substrate, while the other half was flushed with cell media solution. FIGS. 14A&B is a display of photomicrographs taken before (A) and after (B) a selective cell harvest inside the bioreactor. In some cases cells along the midline of the bioreactor would roll up due to the gradient of Trypsin/EDTA normal to the fluid interface. This did not seem to be an issue for long term cell culture. Cells recovered, laid back down, and began to migrate and repopulate the harvested region a few hours after the selective harvest. Residual extracellular matrix is believed to aid in cell recovery and repopulation. Cell number characterization studies were performed as a result of the integration of the miniature bioreactor system with a microfluidics cytometry platform. Verification of cell counts was achieved through comparison with hemocytometer counts and Via-Count (Guava PCA) assays. Cells were inoculated in the bioreactor with $1\times10^5$ cells and allowed to reach approximately 80% confluence. Media was sampled and exchanged daily. Cells were harvested using trypsinization beginning on day 4. Approximately 1-3×105 cells were sampled each time as verified by three cytometry methods as shown in FIG. 15. The results demonstrate good repeatability in cell removal numbers and the ability for the cell culture device to repopulate in a timely fashion for long term cell culture sampling (~48 hours).

Figure 16:
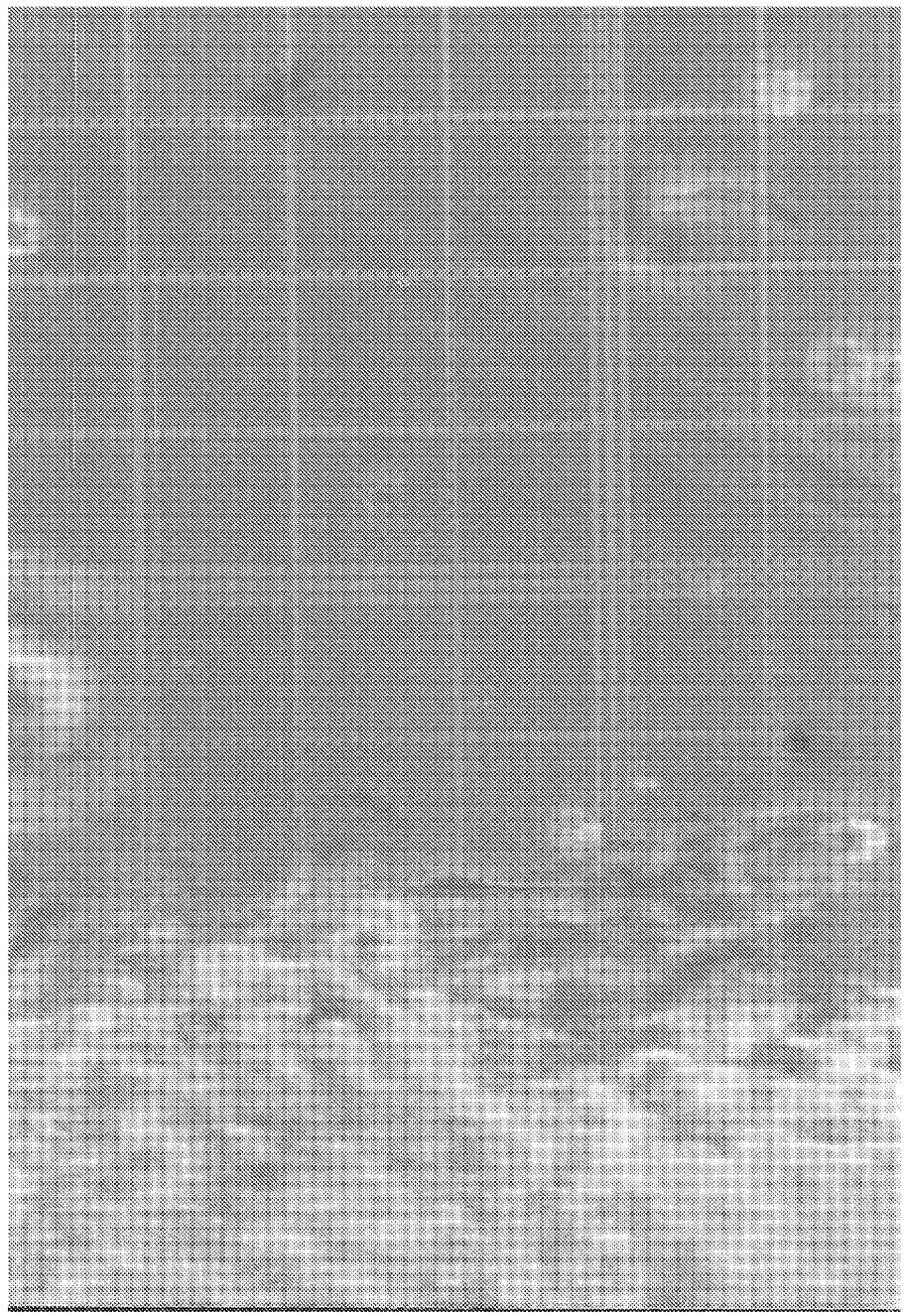
FIG. 16 is a photomicrograph of BHK-21 migration and re-population of the harvested zone of FIG. 14A over a 7 hour period

Referring now to FIG. 16, a microphotograph of the harvested zone after 7 hours of migration and re-population of cells into the harvested zone. This migration and repopulation is evidence that the bioreactors of this invention can be used for moderate and long term culture, where cell are harvested on a continuous, semi-continuous, or periodic (preferred) to support moderate and long cultures while avoiding overpopulation problems.

Hypoxia Studies of Fetal Canine Cardiomyocyte

The bioreactor of FIG. 8 was used to study the effects of hypoxia on fetal cardiomyocytes before and after the injection of stem cells. The study involved 24 hour hypoxia treatments followed by 24 hour re-oxygenation treatments. Once cells in the zones were characterized, stem cells are injected into a stable fetal cardiomyocytes to study paracrine effects, stem cell differentiation and where the stem cells lower apoptotic/necrotic levels. The study also tested stem cell supernatant for paracrine effects.

Experimental Procedures

The experiments included inoculating the zones of the chamber of the bioreactor with fetal canine cardiomyocytes at about $X=5\times10^4$ cells. The cells were then supplied with IMDM medium with 10% FBS and 1% antibiotics. Gas compositions were introduced into the medium feeding the zones. One gas composition was a normal oxygenation gas mixture including 95% air and 5% $CO_2$ supplied from a first gas cylinder containing the gas mixture. To induce hypoxia, a gas mixture including 95% Nitrogen and 5% $CO_2$ is used, which is supplied from a second gas cylinder.

The experimental protocol includes normal culture proliferation for 24 hours followed by photographs to result in cell characterization. After the normal culturing, one of the zones was exposed to hypoxic conditions for 24 hours and photographed. After hypoxic treatment, the hypoxic cells are re-oxygenated for 24 hours and photographed. The cells were then in situ stained for morphological studies. The staining method included ethidium bromide (EB) and acridine orange (AO) in IMDM medium at 0.2 µM levels.

Figure 17:
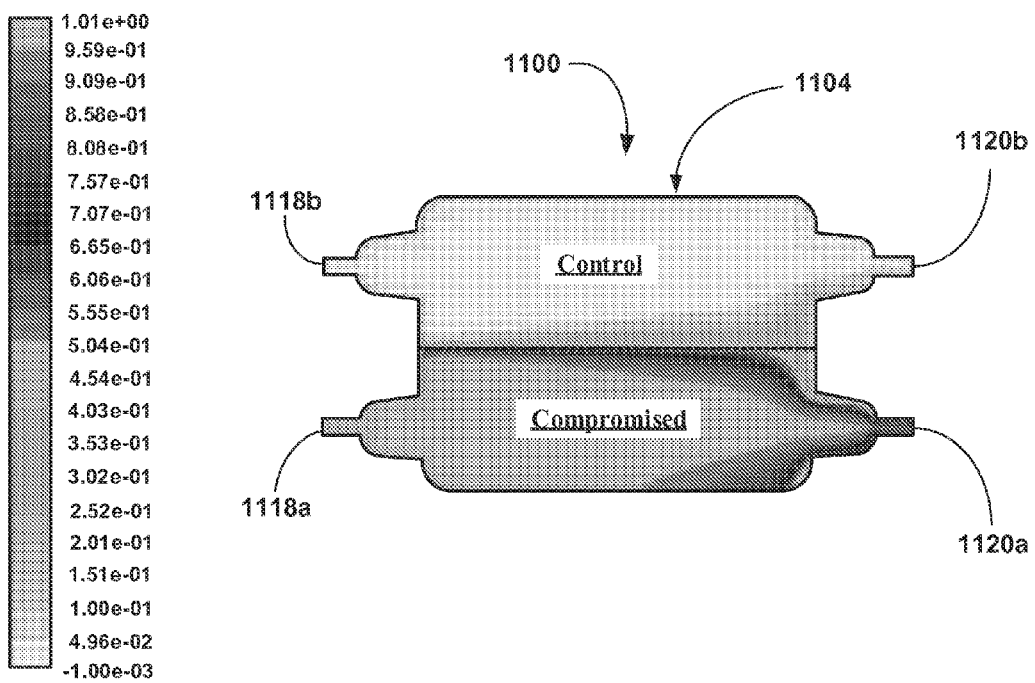
FIG. 17 depicts a simulation of hypoxia exposure of fetal cardiomyocytes in one of the zones of a chamber of FIGS. 2A&B.

Fetal cardiomyocytes were inoculated into both of the zones of the chamber of the bioreactor. Hypoxia was induced in one of the zones by introducing a gas mixture of 95% nitrogen and 5% carbon dioxide, while the other zone was exposed to a standard oxygen rich gas mixture of 95% oxygen and 5% carbon dioxide. The hypoxia introduction permeates the chamber as shown in FIG. 17, where the lower zone evidences the simulated concentration gradient front for hypoxia induction in the lower zone, with little exposure of the control zone on top.

Referring now to FIGS. 18A-F, a series of microphotographs showing the proliferation of fetal cardiomyocytes cells in the zone of the chamber of the bioreactor of FIG. 8. The photographs clearly show that after 72 hours of culturing in the bioreactor, the zones are well populated with the fetal cardiomyocytes. All photo-micrographs were captured using a Nikon TMS phase contrast microscope.

Figure 19A:
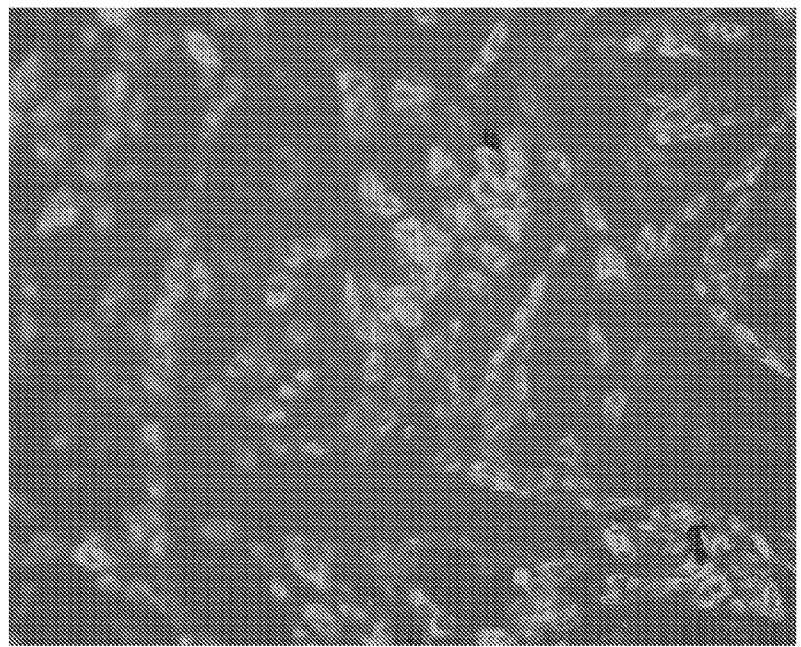
FIGS. 19A&B depict microphotograph of dye assay showing live cells and apoptotic cells after 72 hours of Normoxia: A. Acridine orange stained cells viewed using a 490/530,640/B, IB filter and B. Ethidium bromide stained cells viewed using a 545/605/G, IG filter.

Referring now to FIG. 19A, a dye assay of live fetal cardiomyocytes shows well organized nuclei evidenced by the signature green fluorescence from acridine orange (AO) staining viewed through a 490/503,640/B,IB filter.

Figure 19B:
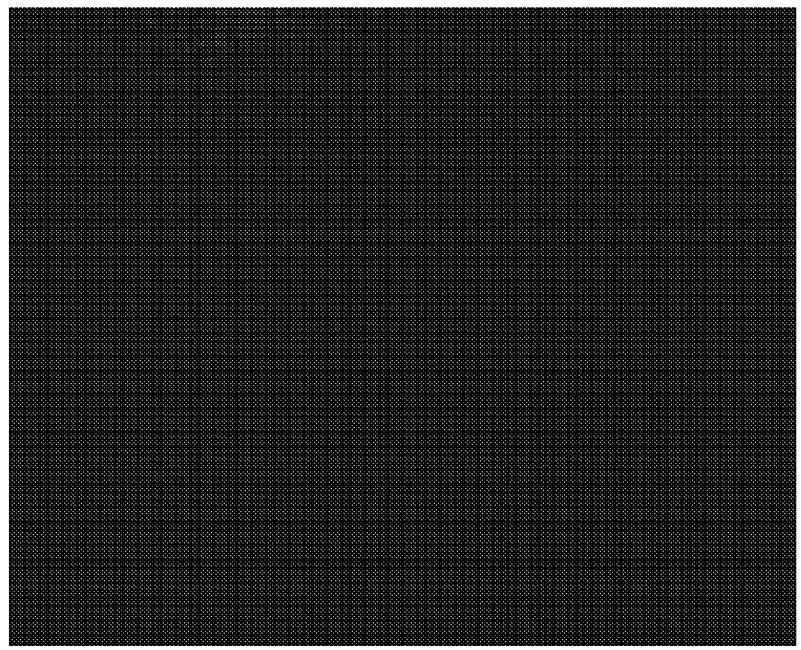

Referring now to FIG. 19B, a dye assay of apoptotic cells or necrotic cells shows no cellular structures evidenced by no signature fluorescence from ethidium bromide (EB) staining viewed through a 545/605/G,IG filter.

Figure 20A:
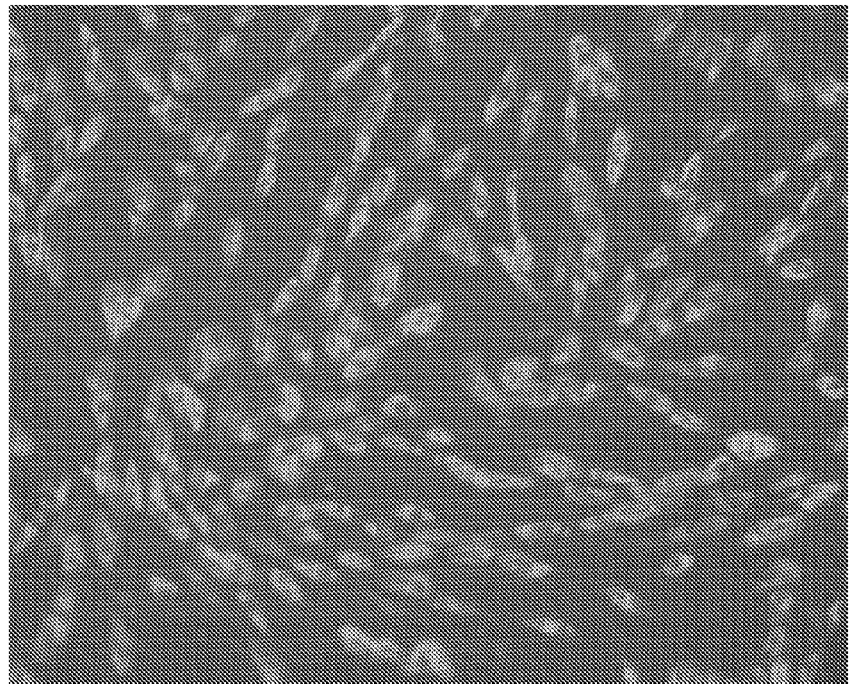
FIG. 20A-D depict microphotograph of dye assay showing results after 24 hours of hypoxia and reoxygenation: A. Acridine orange stained cells viewed using a 490/530,640/B, IB filter and B. Ethidium bromide stained cells viewed using a 545/605/G, IG filter. C. Merged images of A and B. D. Cell quantification.
Figure 20B:
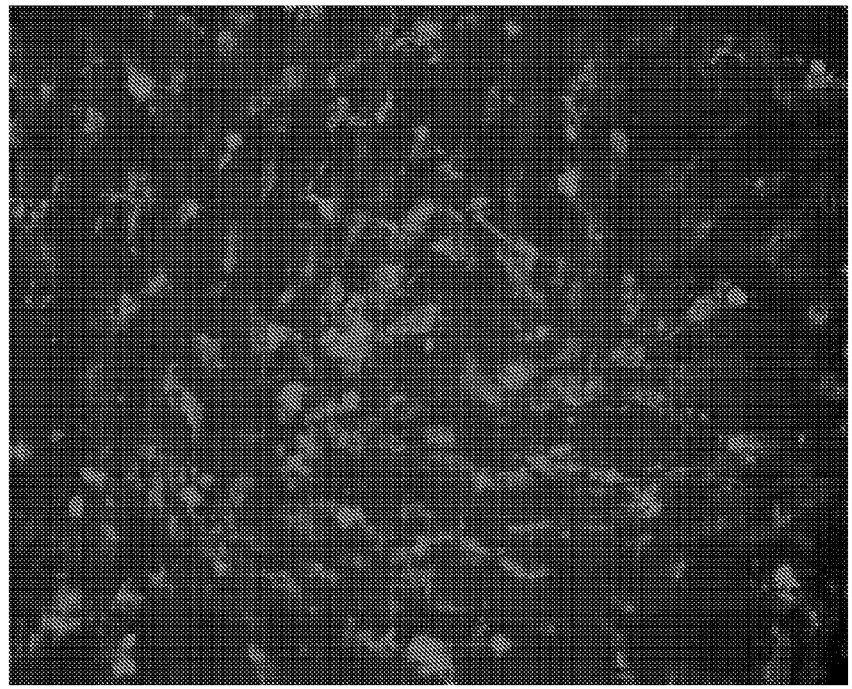
Figure 20C:
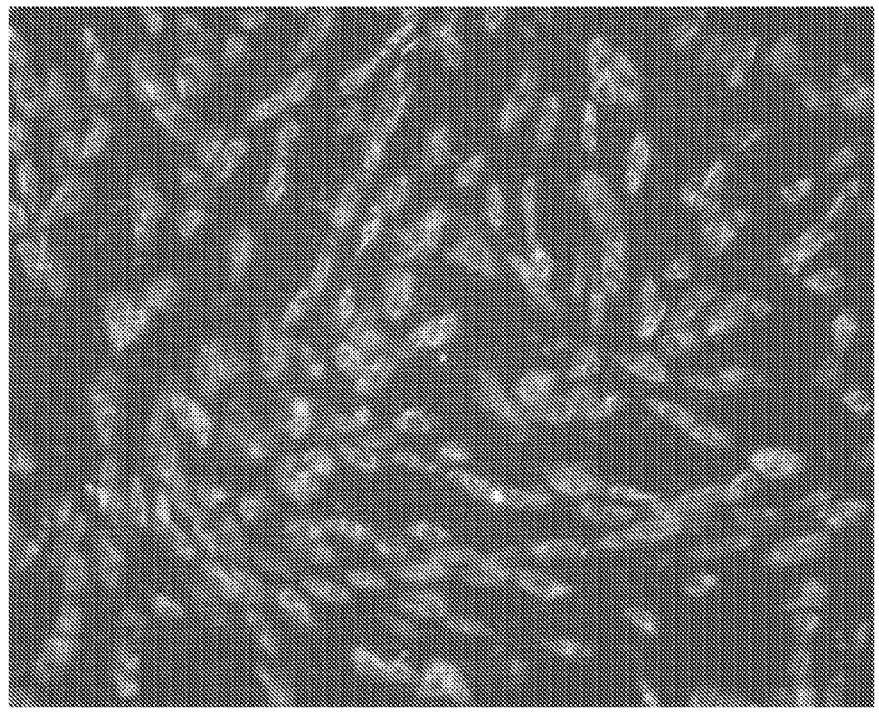
Figure 20D:
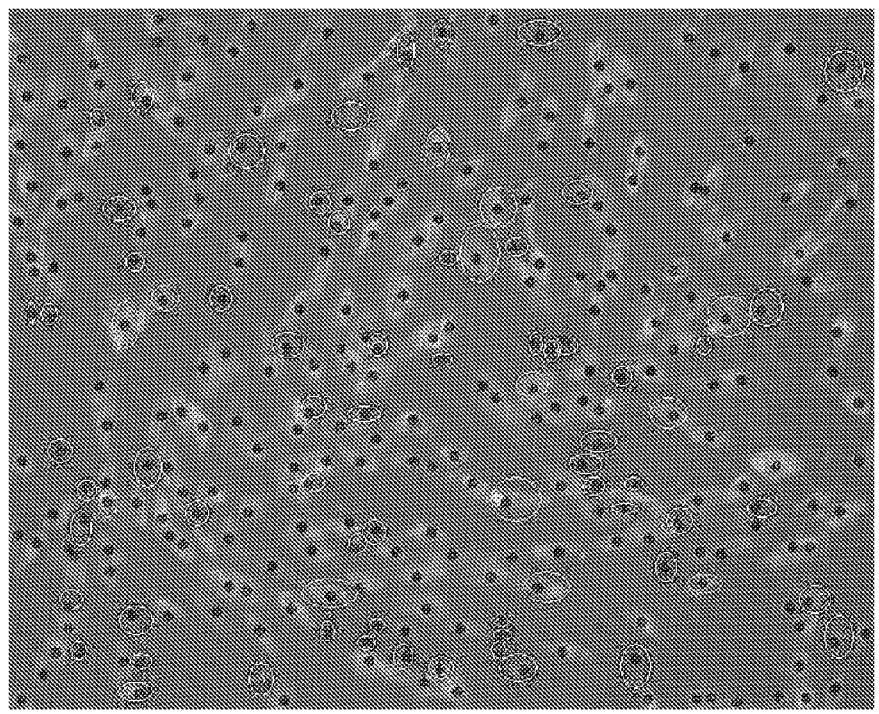

Referring now to FIG. 20A, an image of cells in a zone after 24 hours of hypoxia treatment and 24 hours of re-oxygenation. The image shows the presence of live cells with well defined nuclei as evidenced by the fluorescence from the acridine orange (AO) stained cells. Looking at FIG. 20B, an image of the same area using the ethidium bromide (EB) filter showing dead cells, which appear red in the image. Again, the image is of the cells in the zone after 24 hours of hypoxia treatment and 24 hours of re-oxygenation. Looking at FIG. 20C, a merged image of the images of FIGS. 20A&B. This merged image shows that live cells and dead cells. Looking at FIG. 20D, a cell quantification analysis is shown based on the merged image.

Figure 21A:
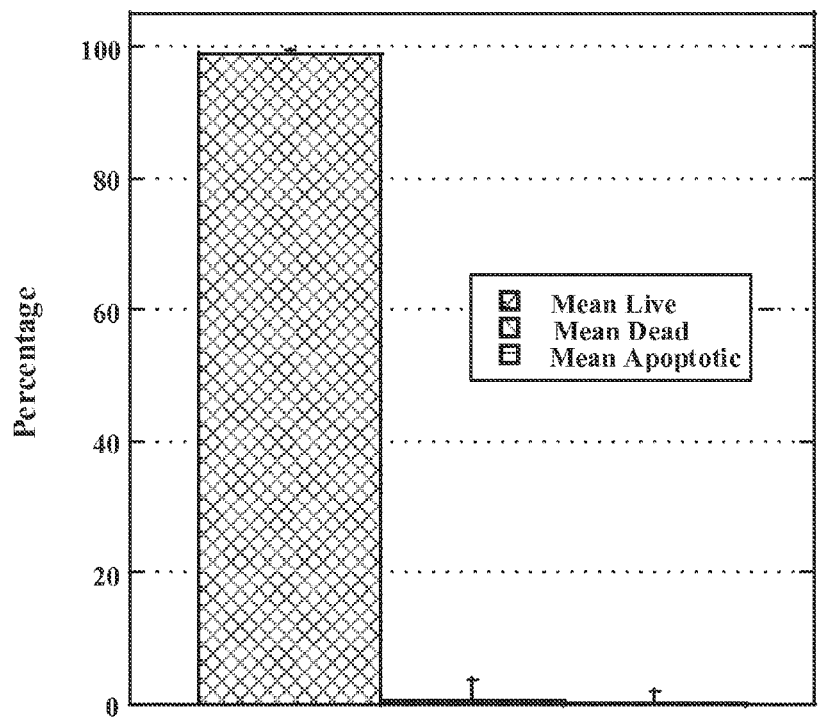
FIGS. 21A&B depict quantification studies after 24 hour hypoxia: A. normal zone and B. hypoxia zone after 24 hours of hypoxia.
Figure 21B:
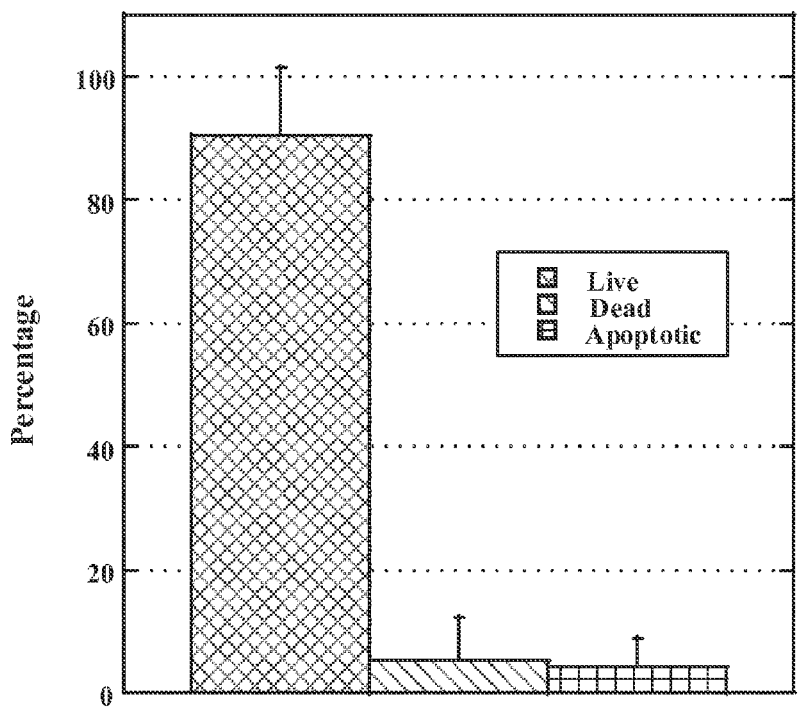

Referring now to FIGS. 21A&B, two cell quantifications are shown after 24 hour hypoxia treatment, one analysis represents a cell quantification in the normal region and one analysis represents a cell quantification in the hypoxia region. Graphs of percentage of total cells from photomicrographs (n=3) of live, dead, and apoptotic cells after 24 hours of hypoxia treatment in the hypoxia region. Error bars are experimental values given as mean and SEM. Since the exp. set is small a student t test is employed for correction.

Figure 22A:
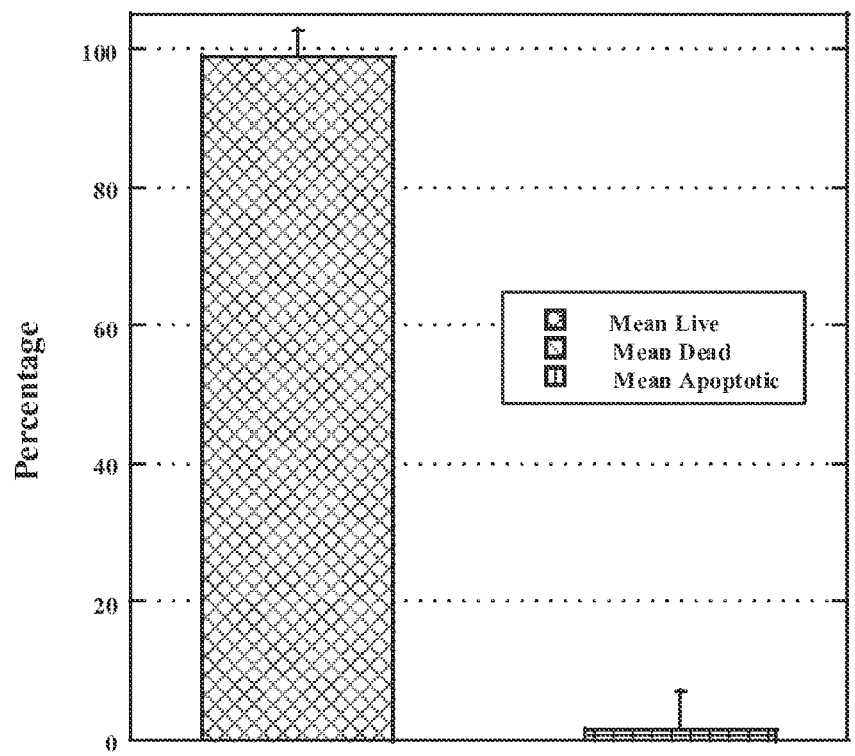
FIGS. 22A&B depict quantification studies after 24 hours reoxygenation: A. After 24 hours reoxygenation of normoxitc region and B. After 24 hours reoxygenation of hypoxic zone.
Figure 22B:
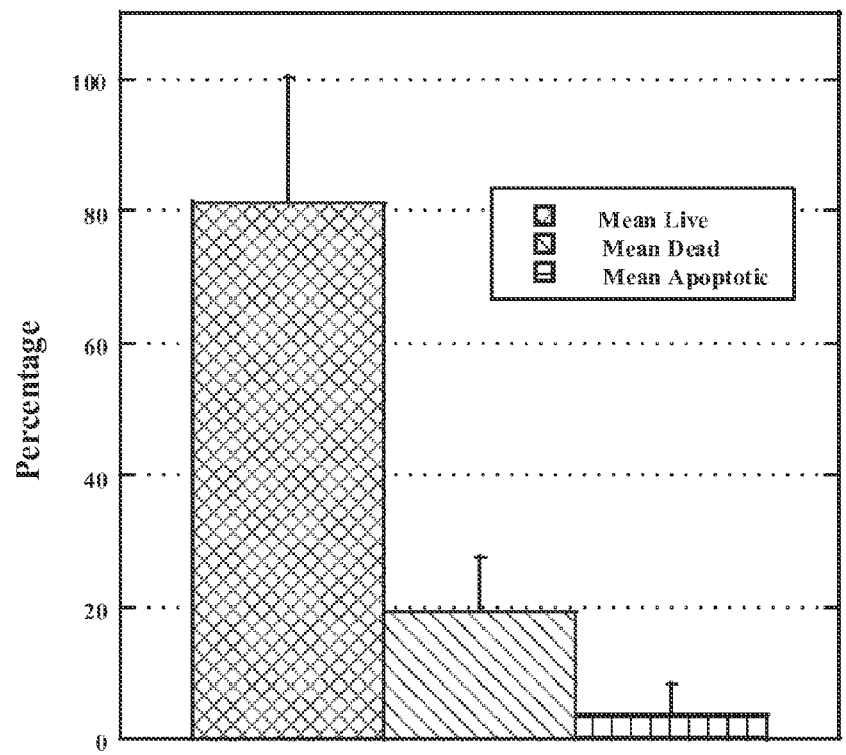

Referring now to FIGS. 22A&B, two cell quantifications are shown after 24 hour re-oxygenation treatment of the cultures of FIGS. 21A&B, one analysis represents a cell quantification in the normal region and one analysis represents a cell quantification in the re-oxygenation of the hypoxia treated region. Graphs of % of total cells from photomicrographs (n=3) of live, dead, and apoptotic cells after 24 hours of reoxygenation. Error bars are experimental values given as mean and SEM. Since the experimental set is small a student t test is employed for correction.

Figure 23:
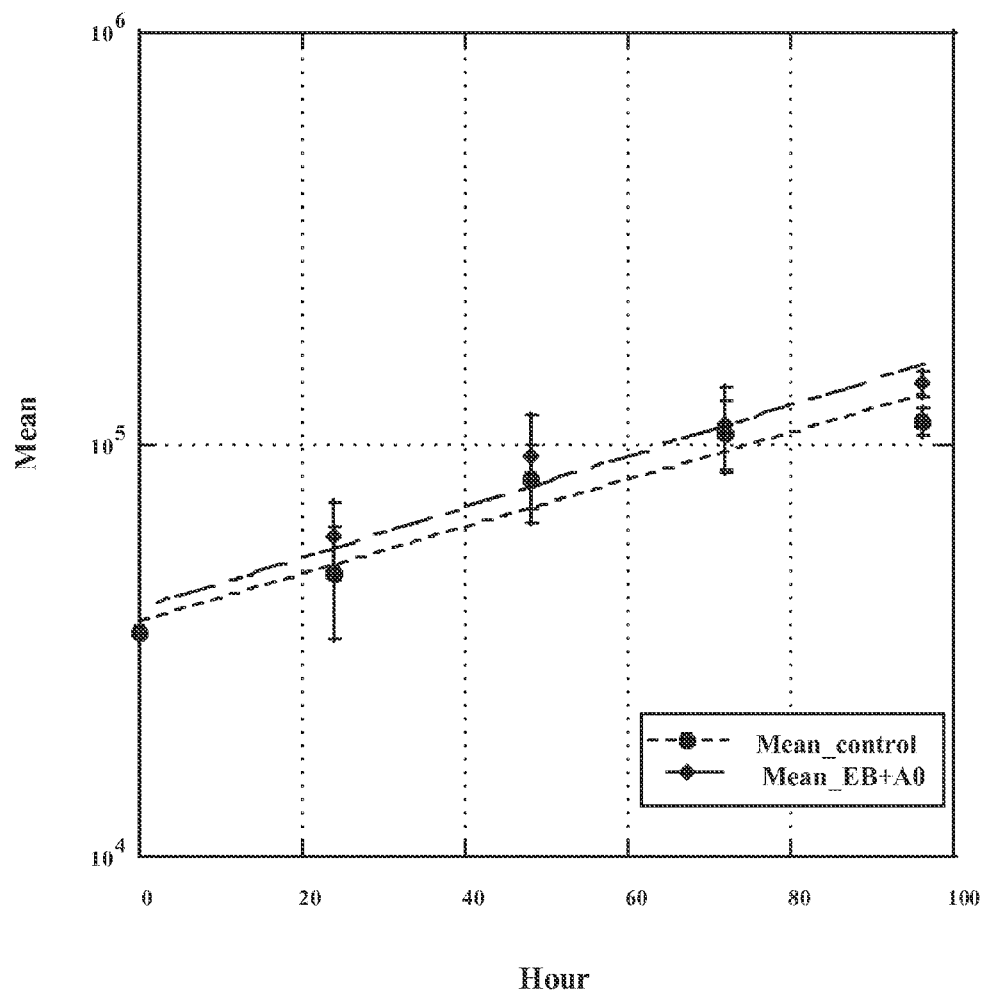
FIG. 23 depicts a plot of Canine Fetal Cardiomyocytes growth in the presence of Acridine Orange and Ethidium Bromide.

Referring now to FIG. 23, shows the growth rate of fetal canine cardiomyocytes in the presence of AO & EB showing that the two dye treatments have little affect on normal cell proliferation as compared to the control.

The hypoxia studied set forth above demonstrates that the bioreactors of this invention are ideal for simulating short, moderate and long term effects of hypoxia or the effects of other conditions that subject cells to a stress. Because the cultures can be exposed to conditions that are similar to what heart tissue may experience during a myocardial infarction, then the bioreactor can be used to study treatment options, such as stem cell inoculation to the hypoxic region (a region after hypoxia treatment). Thus, fetal myocardial cell are inoculated into two zone of the chamber of a bioreactor of FIG. 8 and hypoxia is induced into one zone by introducing a gas composition to the zone to starve the zone of oxygen. Because the other zone is being feed an oxygen rich gas composition, some gas exchange from one zone to the other zone may occur, but such is similar to what actually transpires in the heart. After hypoxia treatment, stem cells can be introduced into the hypoxia treated zone or into both zones. The effects of the stem cell introduction can be monitoring visually using a light microscope, using active dyes, or analyzing cell products. Stem cell introduction follows the same pattern as shown in FIG. 17.

References Cited In The Invention

The following references were cited in the specification:
1. Goodwin, T. J., Jessup J M, Wolf, D A, Spaulding G F, 1993. Reduced Shear Stress: a major component in the ability of mammalian tissues to form three-dimensional assemblies in simulated microgravity. J Cell Biochem 51:304-311.
2. Levesque, M. J. and Nerem, R. M. 1985, —The elongation and orientation of cultured endothelial cells in response to shear stress." Journal of Biomechanical Engineering. Vol. 107, pp. 341-347.
3. Jacobson, S. C. Hergenröder, R., Koutny, L. B., Ramsey, J. M., Anal. Chem. 1994, Vol. 66. pp. 4184-4189.

All references cited herein are incorporated by reference. Although the invention has been disclosed with reference to its preferred embodiments, from reading this description those of skill in the art may appreciate changes and modification that may be made which do not depart from the scope and spirit of the invention as described above and claimed hereafter.

We claim:
1. An apparatus for growing cells comprising:
a laminar flow chamber including:
  a plurality of inlets disposed in a first end of the chamber, where each inlet includes a diffuser, and
  a corresponding plurality of outlets disposed in a second end of the chamber, where each outlet includes a collector,
where the inlets on the first end of the chamber are aligned with the outlets on the second end of the chamber, where fluid flowing through the inlets establishes substantially separated, parallel laminar flow zones within the chamber between the inlets and the aligned outlets, and where the chamber includes no physical barriers separating the laminar flow zones, a fluid handling system including:
  a liquid handling subsystem including:
    at least one inlet valve, and
    at least one outlet valve,
      where the at least one inlet valve is connected to the chamber inlets for supplying medium to the zones of the chamber and the at least one outlet valve is connected to the chamber outlets directing spent fluid from the zones to a waste container, a cell collecting container, or a medium recycle conduit a gas permeable membrane forming a top surface or bottom surface of the zones,
  a controlled gas chamber assembly disposed above the top surface or below the bottom surface including:
    side walls,
    a gas impermeable top,
    an open bottom,
    a gas chamber defined by the wall, the top and the permeable membrane of the zones,
    a gas inlet connected to a gas supply and
    a gas outlet connected to a vent,
      where the assembly is adapted to circulate a gas composition into the chamber through the inlet and out of the outlet at a rate sufficient to permit the gas composition to be transported into the zones and exchanged from the zones, and
  a gas handling subsystem having:
    gas supply,
    at least one inlet valve, and
    gas regulator,
      where the gas handling subsystem supplies gas at a controlled rate to the gas chamber.

2. The apparatus of claim 1, wherein each zone includes: a substrate disposed on a top or bottom of the zone.

3. The apparatus of claim 2, wherein the substrate is a cell conducive substrate.

4. The apparatus of claim 2, wherein the substrate is transparent to light of a desired region of the electromagnetic spectrum.

5. The apparatus of claim 1, wherein the gas handling subsystem includes:
  a gas in-line introduction subsystem including at least one bubble trap and at least one gas exchanger adapted to introduce a gas composition directly into the medium before the medium enters the inlets of the chamber.

6. The apparatus of claim 5, wherein the gas in-line introduction subsystem includes:
  a bubble trap for each zone and
  a gas exchanger for each zone.

7. The apparatus of claim 1, further comprising:
  a medium reservoir connected to the at least one inlet valve,
  a harvesting agent reservoir connected to the at least one inlet valve, and
  an additive reservoir connected to the at least one inlet valve,
    where the reservoirs are adapted to supply medium to the zones for feeding, harvesting or stressing the cells in the zones.

8. The apparatus of claim 1, wherein the cells are selected from the group consisting of prokaryotic cells, eukaryotic cells, stem cells, and mixtures or combinations thereof.

9. A method of culturing cells comprising the steps of:
  providing a laminar flow bioreactor comprising:
    a laminar flow chamber including:
      a plurality of laminar flow zones, each zone including:
        an inlet having:
          a diffuser, and
        an outlet having:
          a collector;
    a fluid handling system including:
      a liquid handling subsystem adapted to supply a medium to the zones and including:
        at least one inlet valve, and
        at least one outlet valve;
      a medium reservoir connected to the at least one inlet valve;
      a harvesting agent reservoir connected to the at least one inlet valve;
      an additive reservoir connected to the at least one inlet valve;
      a waste container connected to the at least one inlet valve;
      a cell collecting container connected to the at least one inlet valve;
      optional medium recycle conduit connected to the at least one inlet valve;
      a gas handling subsystem adapted to supply gas to the zones and including:
        a gas permeable membrane forming a top surface or bottom surface of the zones,
          a controlled gas chamber assembly disposed above the top surface or below the bottom surface including:
            side walls,
            a gas impermeable top,
            an open bottom,
            a gas chamber defined by the wall, the top and the permeable membrane of the zones,
            a gas inlet connected to a gas supply and
            a gas outlet connected to a vent,
              where the assembly is adapted to circulate a gas composition into the chamber through the inlet and out of the outlet at a rate sufficient to permit the gas composition to be transported into the zones and exchanged from the zones;
  inoculating each zone of the chamber with the same or different cells;
  growing the inoculated cells to a desired population in each zone, where the desired cell population is the same or different;
  harvesting a portion of the cell population in each of the zone, when the cells in the zone have grown to its desired cell population; and
  collecting the harvested cells.

10. The method of claim 9, wherein the harvesting step includes the steps of:
  washing the zone to be harvested with saline solution;
  flushing the zone to be harvested with an enzyme treatment to prepare the cells for harvesting; and
  infusing fresh medium into the zone to be harvested,
    where the enzyme treated cells, which are now suspended in the medium in the zone, are wept from the zone for collecting in the collecting step.

11. The method of claim 9, further comprising the step of:
  allowing a remaining cell population to migrate throughout the harvested zone, and
  repeating the growing, harvesting and collecting steps every time the cell population reaches the same or different desired population.

12. The method of claim 11, wherein the harvesting step includes the steps of:
  washing the zone to be harvested with saline solution;
  flushing the zone to be harvested with an enzyme treatment to prepare the cells for harvesting; and infusing fresh medium into the zone to be harvested,
where the enzyme treated cells, which are now suspended in the medium in the zone, are wept from the zone for collecting in the collecting step.

13. A method of culturing cells comprising the steps of:
providing a laminar flow bioreactor comprising:
   a laminar flow chamber including:
      a plurality of laminar flow zones, each zone including:
         an inlet having:
            a diffuser, and
         an outlet having:
            a collector,
   a fluid handling system including:
      a liquid handling subsystem adapted to supply a medium to the zones and including:
         at least one inlet valve and
         at least one outlet valve,
      a medium reservoir connected to the at least one inlet valve;
      a harvesting agent reservoir connected to the at least one inlet valve;
      an additive reservoir connected to the at least one inlet valve;
      a waste container connected to the at least one inlet valve;
      a cell collecting container connected to the at least one inlet valve;
      optional medium recycle conduit connected to the at least one inlet valve;
   a gas handling subsystem adapted to supply gas to the zones and including:
      a gas in-line introduction subsystem comprising:
         a bubble trap for each zone, and
         a gas exchanger for each zone;
      where the bubble traps are adapted to introduce a gas composition into the medium, and the gas exchangers are adapted to permit gas exchange in the medium.
inoculating each zone of the chamber with the same or different cells,
growing the inoculated cells to a desired population in each zone, where the desired cell population is the same or different,
harvesting a portion of the cell population in each of the zone, when the cells in the zone have grown to its desired cell population, and
collecting the harvested cells.

14. The method of claim 13, further comprising the step of:
allowing a remaining cell population to migrate throughout the harvested zone, and
repeating the growing, harvesting and collecting steps every time the cell population reaches the same or different desired population.

* * * * *